United States Patent [19]
Daniel et al.

[11] Patent Number: 6,001,118
[45] Date of Patent: Dec. 14, 1999

[54] DISTAL PROTECTION DEVICE AND METHOD

[75] Inventors: John M. K. Daniel; Thomas E. Broome, both of Hopkins; David J. Holtan, Rogers; Robert L. Cassell, Otsego; Daniel O. Adams, Orono, all of Minn.

[73] Assignee: Scimed Life Systems, Inc., Maple Grove, Minn.

[21] Appl. No.: 08/943,358

[22] Filed: Oct. 3, 1997

Related U.S. Application Data

[63] Continuation-in-part of application No. 08/810,825, Mar. 6, 1997, Pat. No. 5,814,064.

[51] Int. Cl.$^6$ ................................................ A61M 29/00
[52] U.S. Cl. ............................................ 606/200; 606/159
[58] Field of Search ............................... 606/1, 159, 191, 606/192, 194, 198, 200; 604/96–101; 128/599

[56] References Cited

U.S. PATENT DOCUMENTS

| | | |
|---|---|---|
| 4,425,908 | 1/1984 | Simon . |
| 4,590,938 | 5/1986 | Segura et al. . |
| 4,706,671 | 11/1987 | Weinrib . |
| 4,723,549 | 2/1988 | Wholey et al. . |
| 4,728,319 | 3/1988 | Masch . |

(List continued on next page.)

FOREIGN PATENT DOCUMENTS

| | | |
|---|---|---|
| 0 737 450 A1 | 10/1996 | European Pat. Off. . |
| 2821048 | 11/1979 | Germany . |
| 764684 | 9/1980 | U.S.S.R. . |
| 2020557 | 1/1993 | United Kingdom . |
| WO 94/24946 | 11/1994 | WIPO . |
| WO 96/01591 | 1/1996 | WIPO . |

OTHER PUBLICATIONS

*The Journal of Invasive Cardiology,* vol. 8, Supplement E, 1996, "Stents Don't Require Systemic Anticoagulation . . . But the Technique (and Results) Must Be Optimal", by Issaam Moussa, MD, et al., pp. 3E–30E. Health Management Publications, Inc.

(List continued on next page.)

*Primary Examiner*—Michael Buiz
*Assistant Examiner*—William W. Lewis
*Attorney, Agent, or Firm*—Westman, Champlin & Kelly

[57] ABSTRACT

An emboli capturing system captures emboli in a body lumen. A first elongate member has a proximal end and a distal end. An expandable emboli capturing device is mounted proximate the distal end of the first elongate member, and is movable between a radially expanded position and a radially contracted position. When in the expanded position, the emboli capturing device forms a basket with a proximally opening mouth. A second elongate member has a proximal and a distal end with a lumen extending therebetween. The lumen is sized to slidably receive a portion of the first elongate member. An expandable delivery device is mounted to the distal end of the second elongate member and is movable from a radially retracted position to a radially expanded position. The delivery device has a receiving end configured to receive the emboli capturing device, and retains at least the mouth of the emboli capturing device in a radially retracted position.

30 Claims, 16 Drawing Sheets

U.S. PATENT DOCUMENTS

| | | |
|---|---|---|
| 4,790,812 | 12/1988 | Hawkins, Jr. et al. . |
| 4,790,813 | 12/1988 | Kensey . |
| 4,794,928 | 1/1989 | Kletschka . |
| 4,873,978 | 10/1989 | Ginsburg . |
| 4,926,858 | 5/1990 | Gifford, III et al. . |
| 5,011,488 | 4/1991 | Ginsburg . |
| 5,071,407 | 12/1991 | Termin et al. . |
| 5,100,423 | 3/1992 | Fearnot . |
| 5,108,419 | 4/1992 | Reger et al. . |
| 5,190,546 | 3/1993 | Jervis . |
| 5,329,942 | 7/1994 | Gunther et al. . |
| 5,376,100 | 12/1994 | Lefebvre . |
| 5,421,832 | 6/1995 | Lefebvre . |
| 5,549,626 | 8/1996 | Miller et al. . |
| 5,695,519 | 12/1997 | Summers et al. |

OTHER PUBLICATIONS

"A New Percutaneous Vena Cava Filter", by Andrew Cragg et al., *AJR,* 141, Sep. 1983, pp. 601–604.

"Nonsurgical Placement of Arterial Endoprosthesis: A New Technique Using Nitional Wire", by Andrew Cragg et al., *AJR,* Apr. 1983, pp. 261–263.

"Long–Term Patency of the Ductus Arteriosus After Balloon Dilatation: An Experimental Study", by Gunnar Lund, M.D., et al., *AJR,* Sep. 1983;, p. 772.

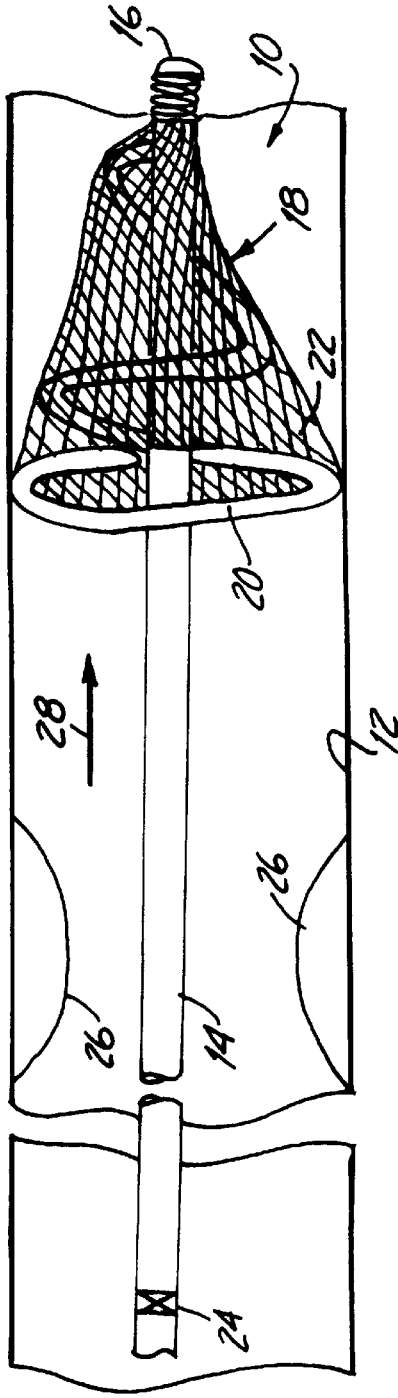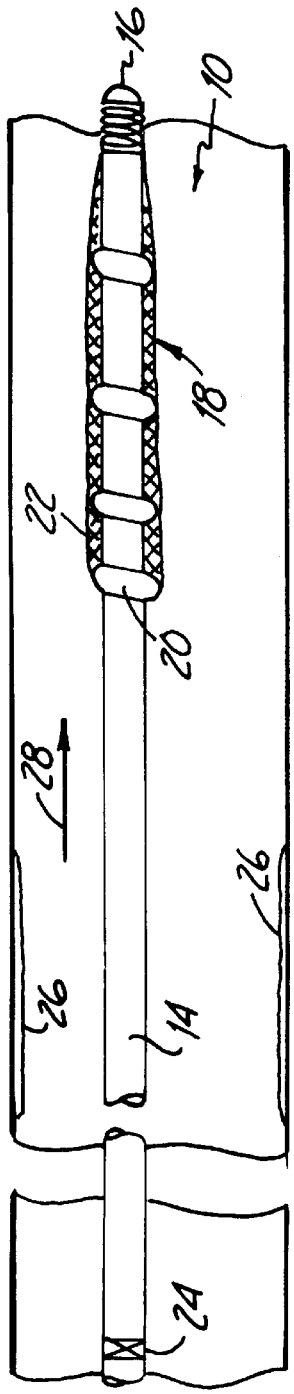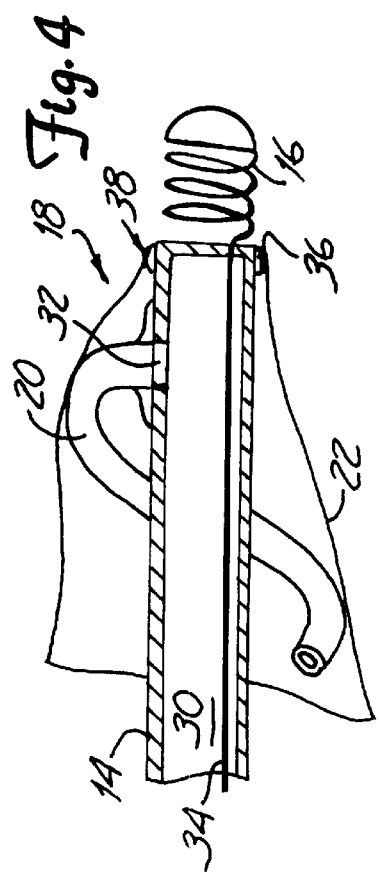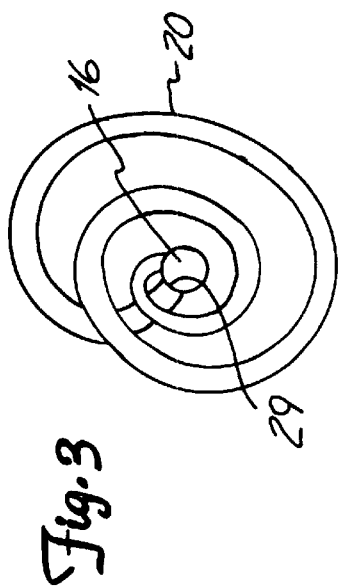

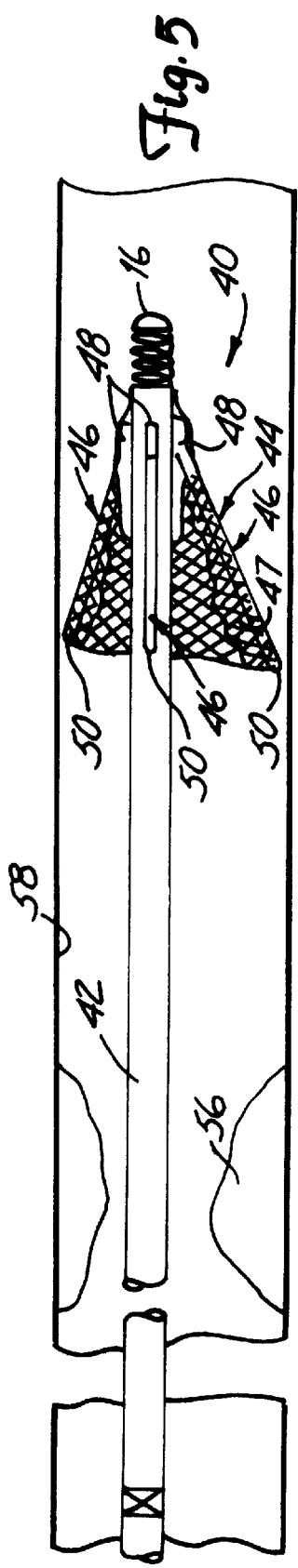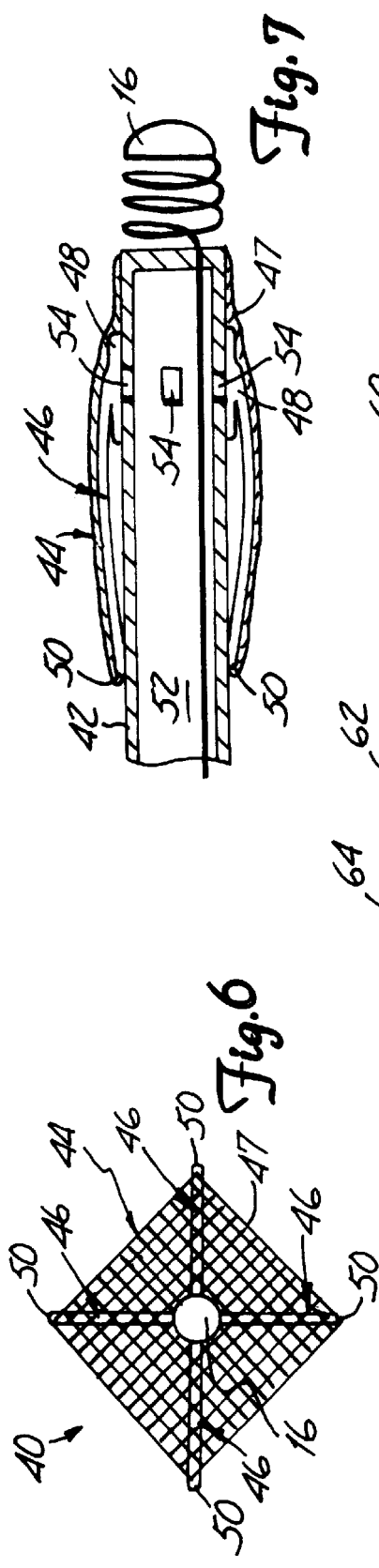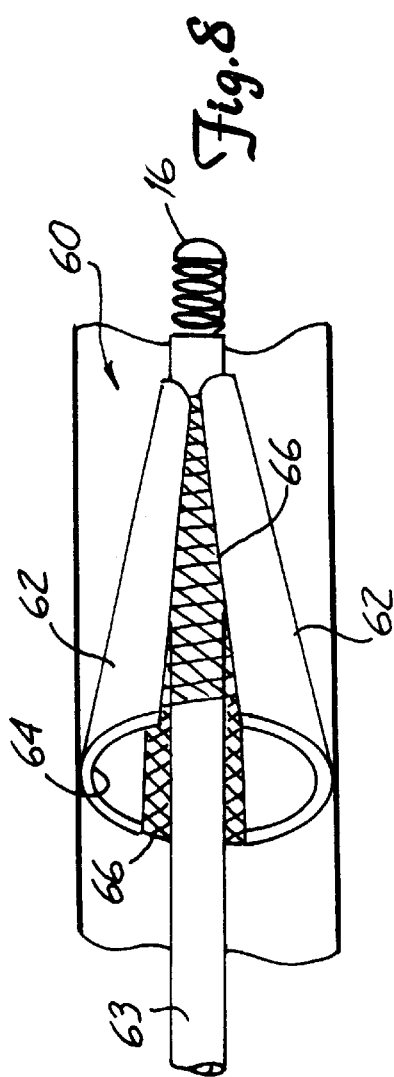

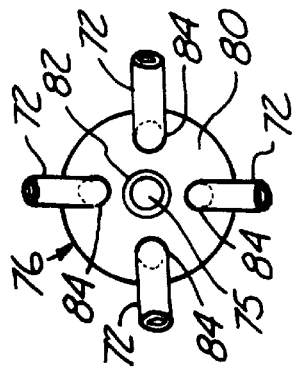
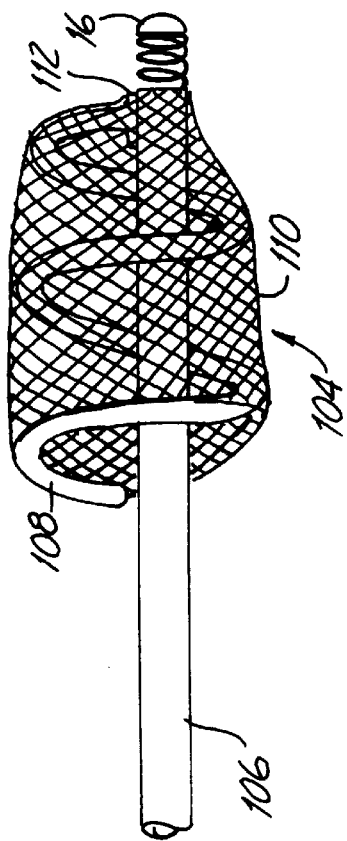
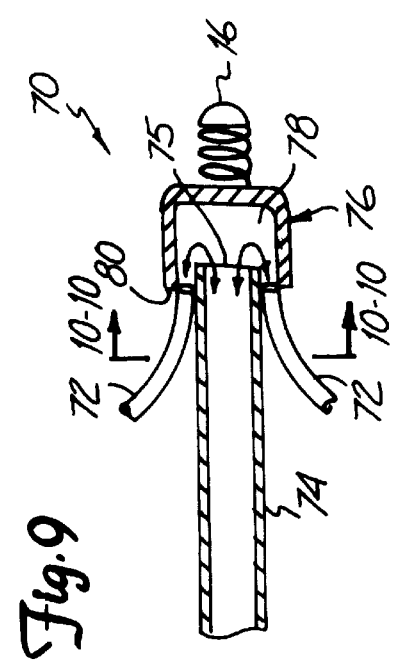
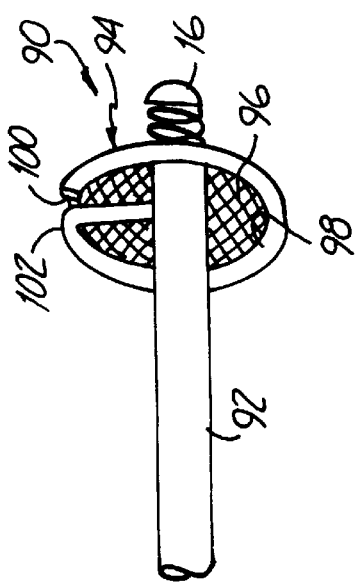

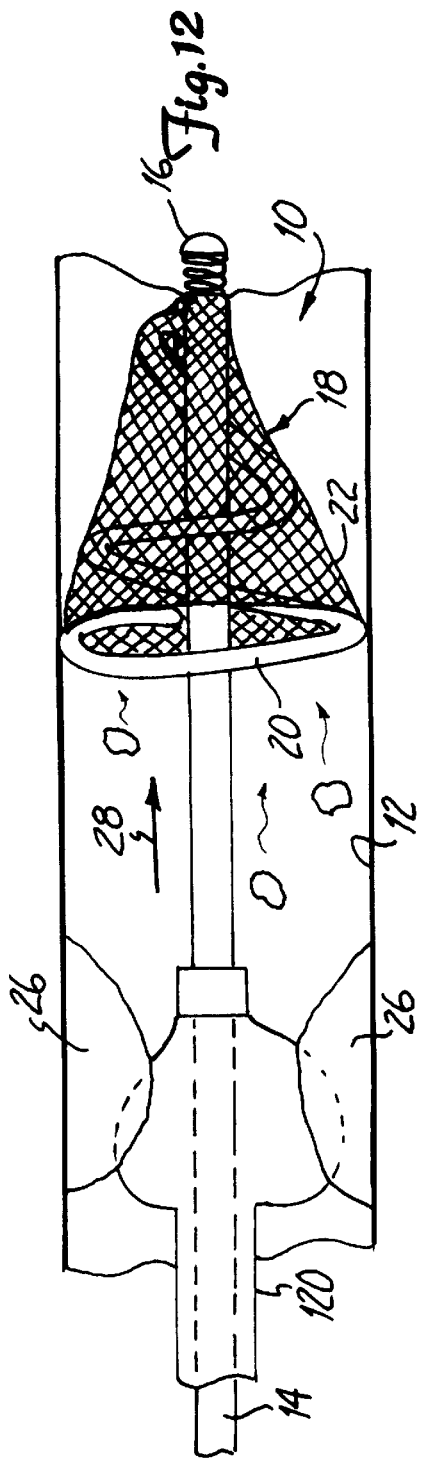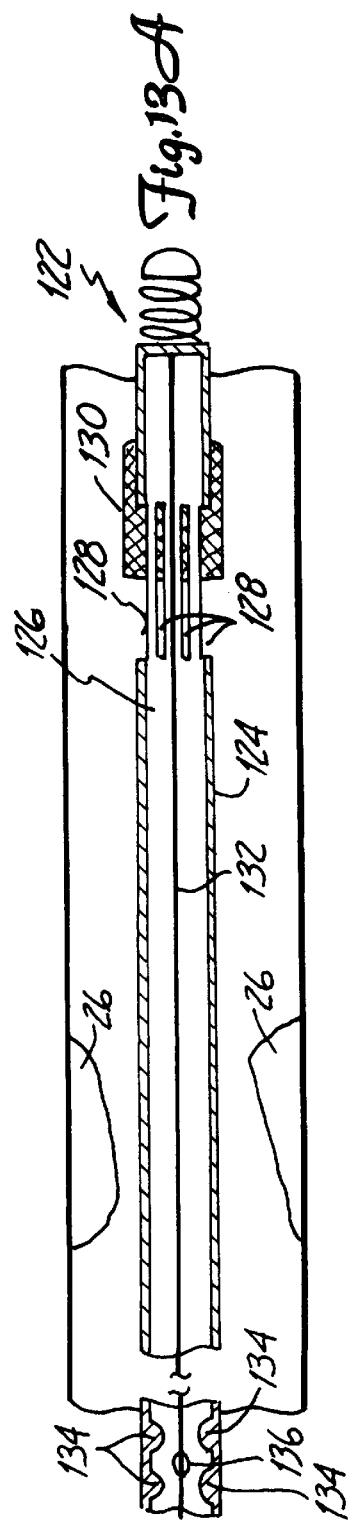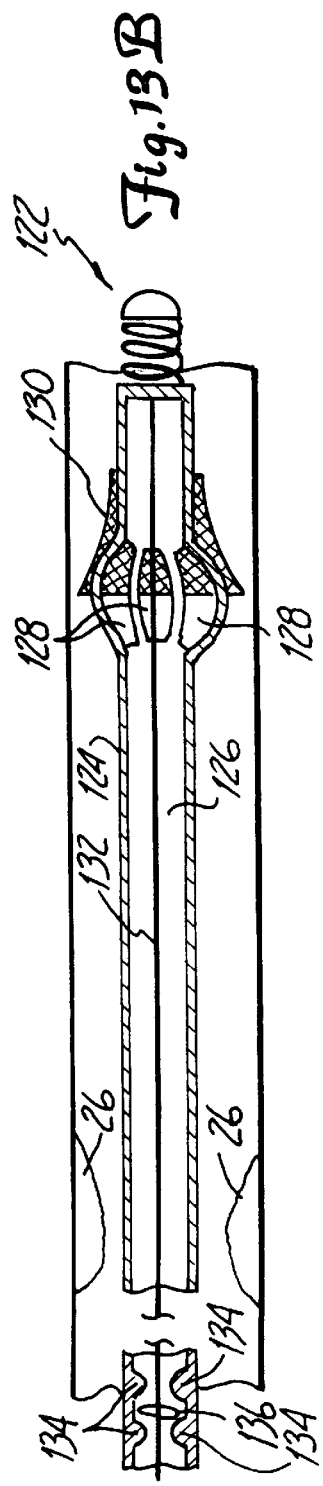

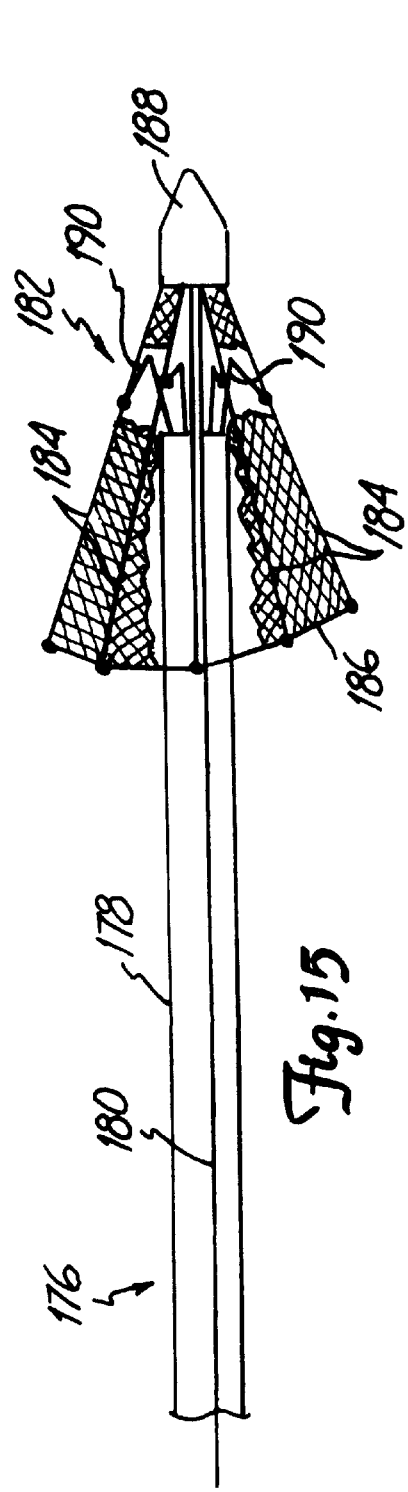
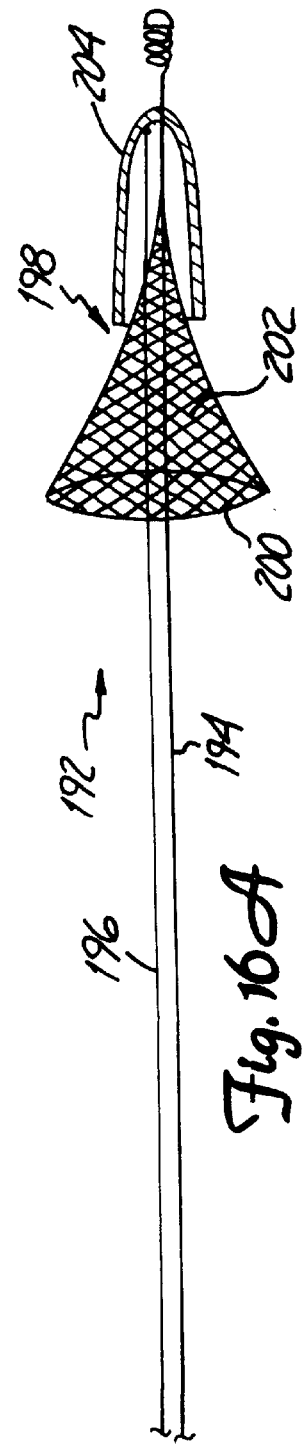
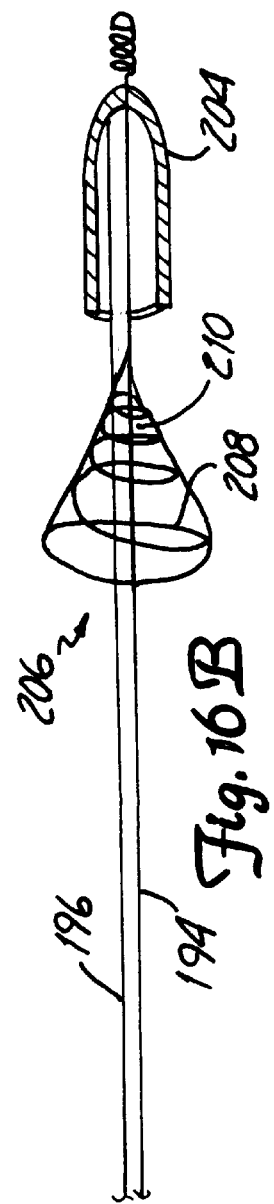
Fig. 15
Fig. 16A
Fig. 16B

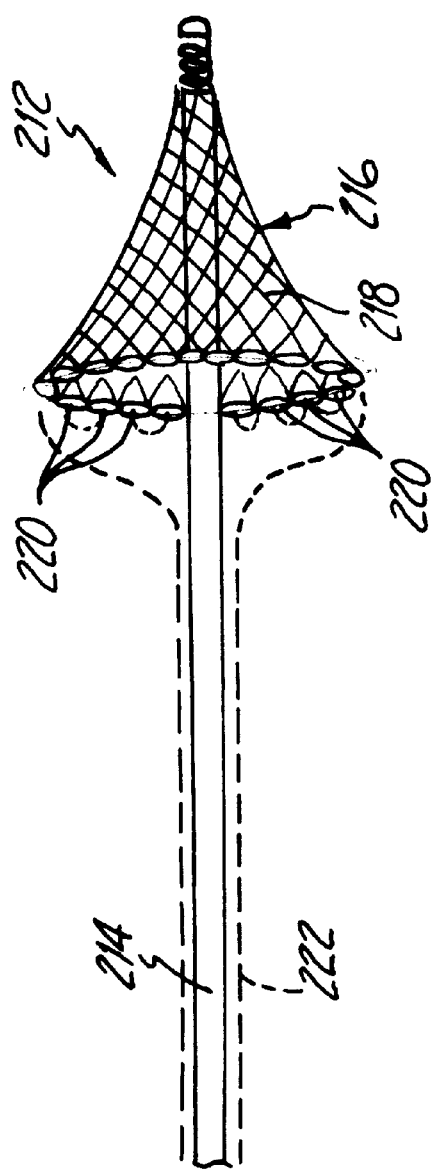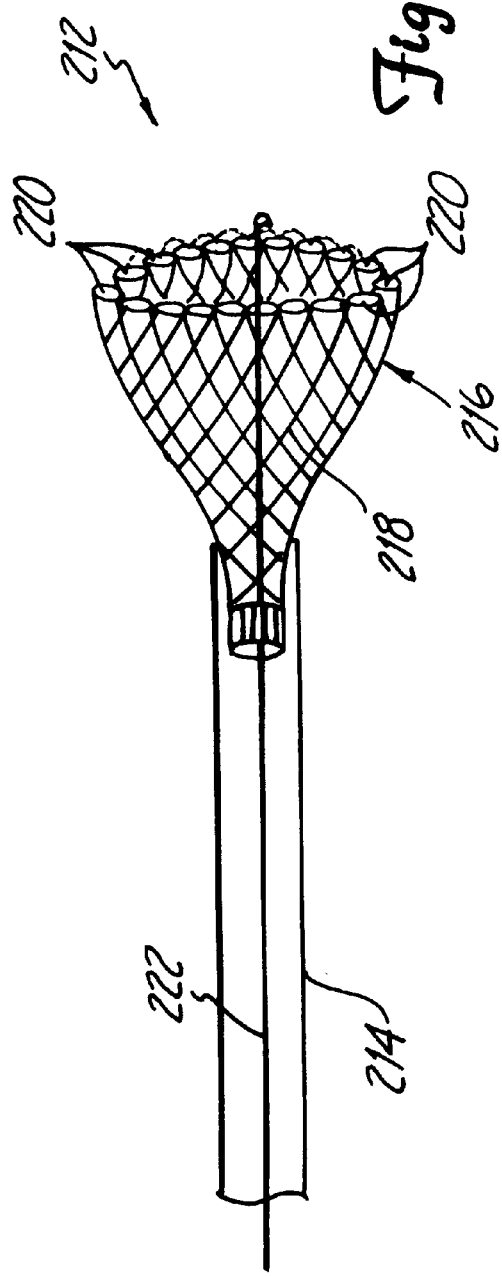

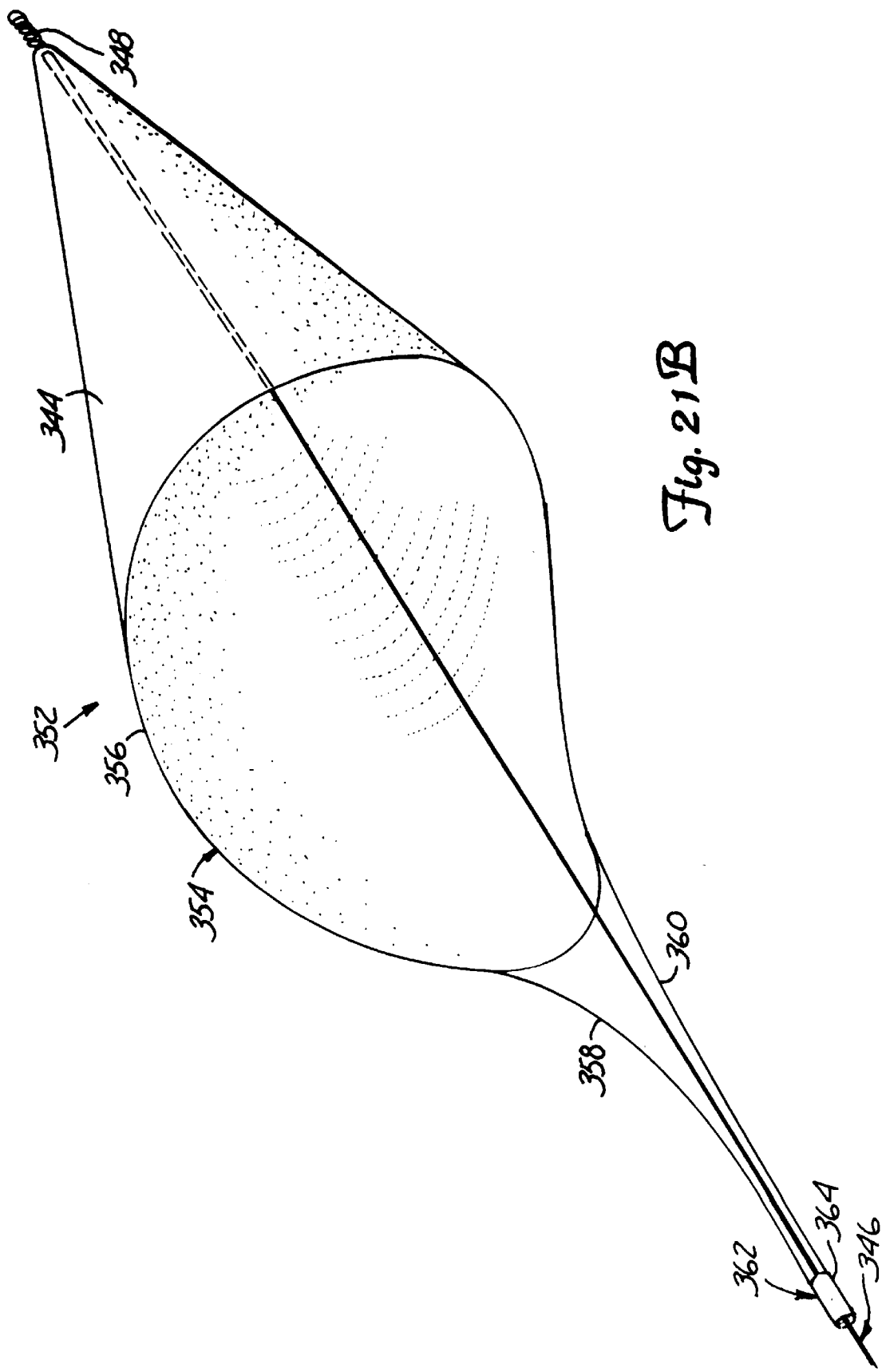

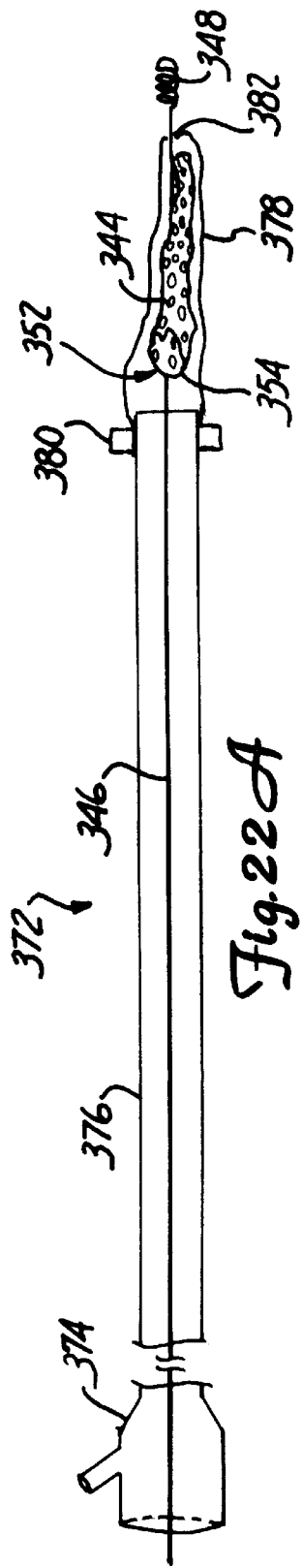
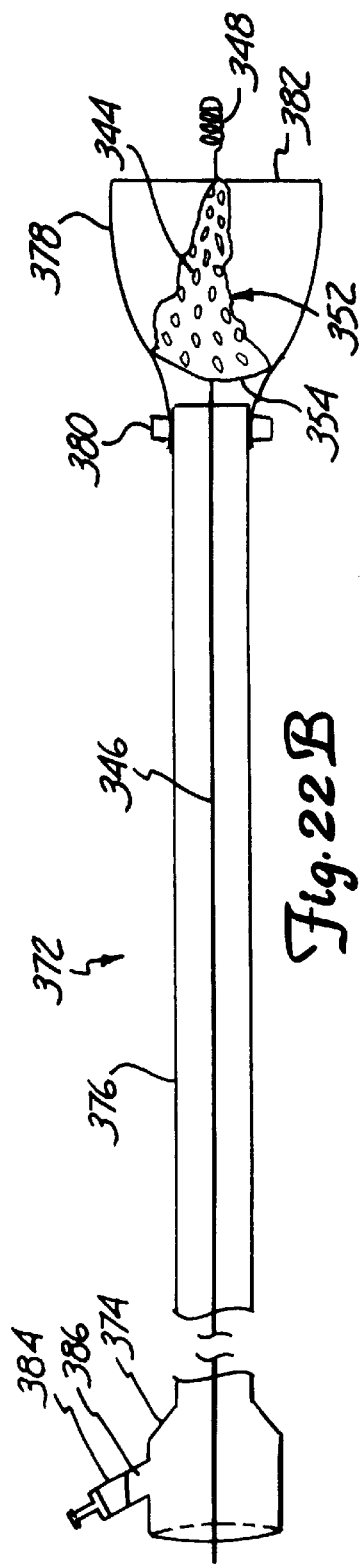
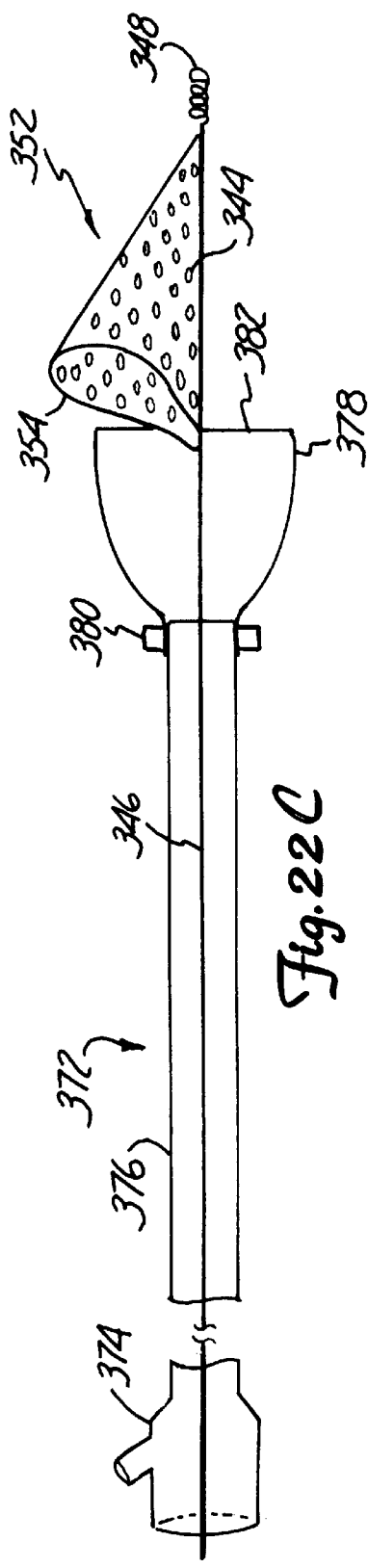

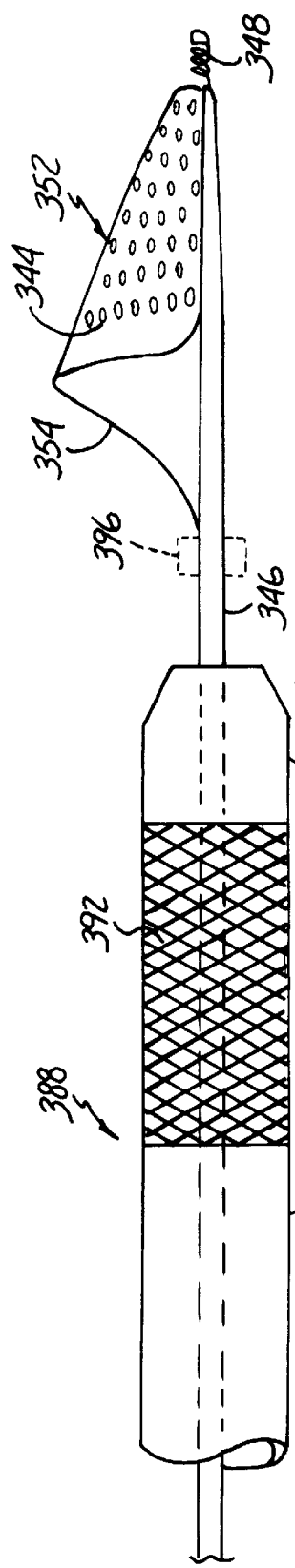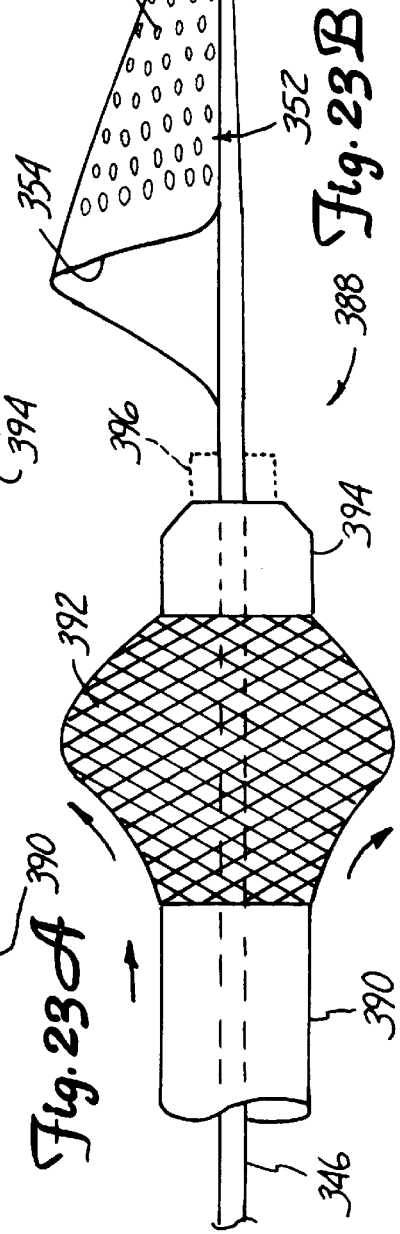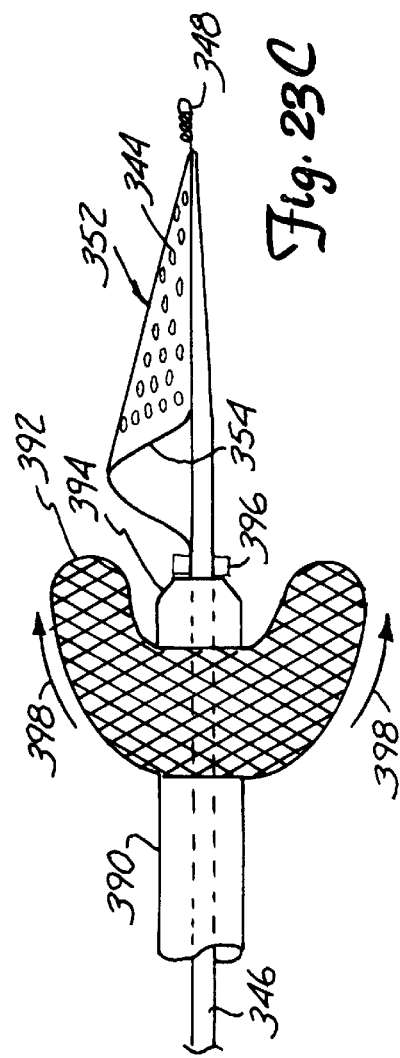

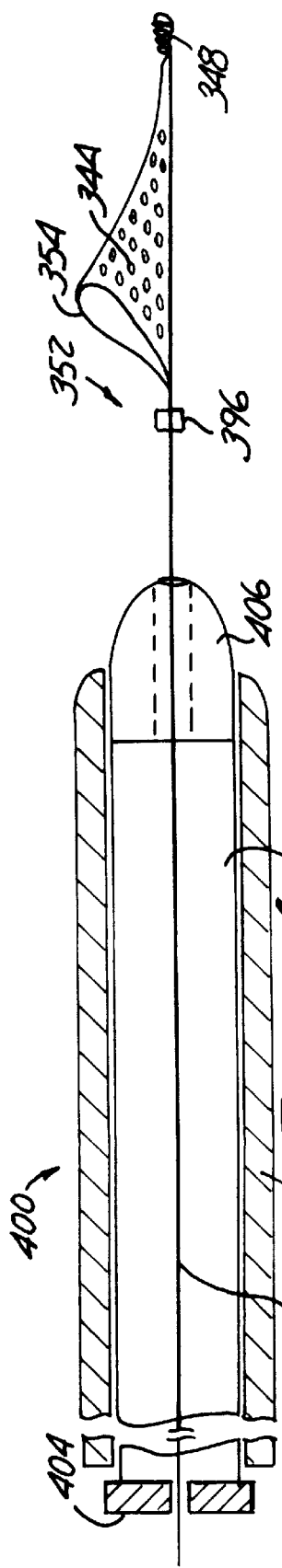
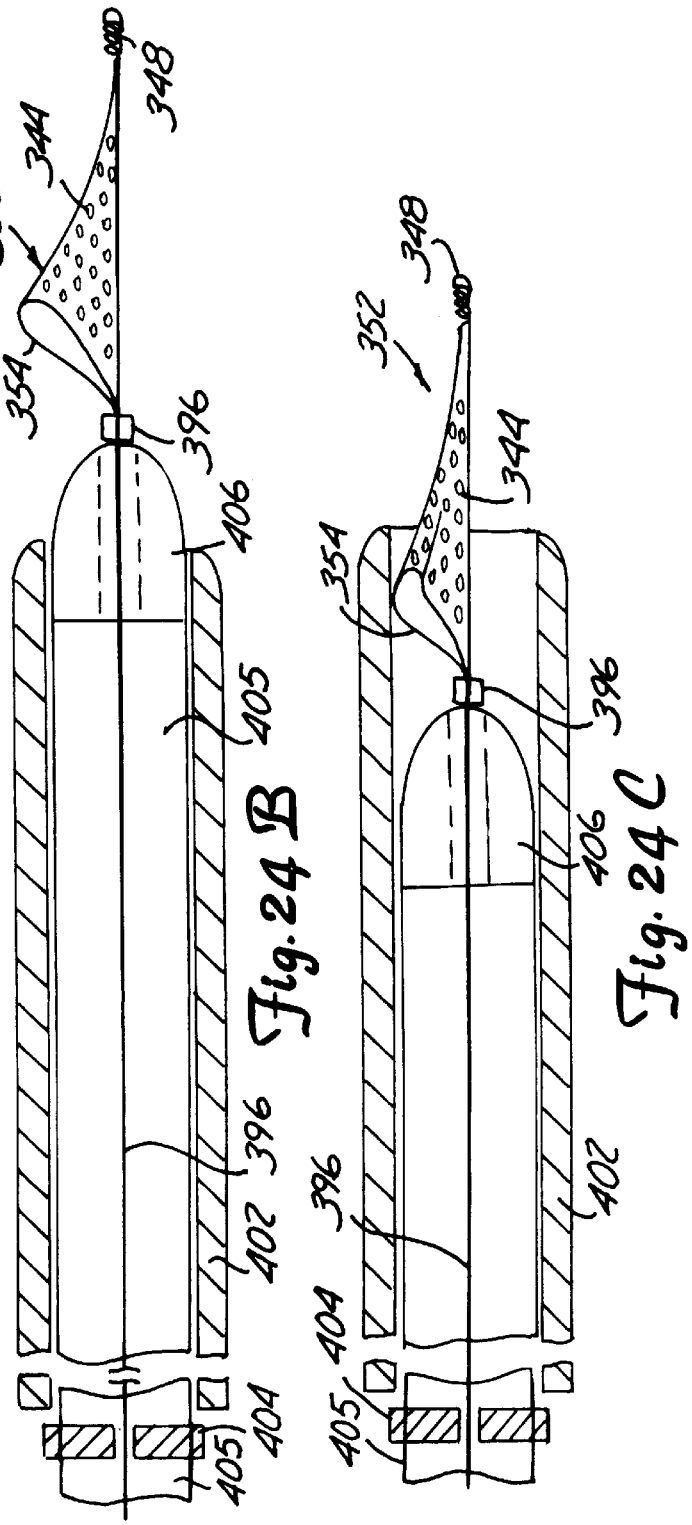

DISTAL PROTECTION DEVICE AND METHOD

INCORPORATION BY REFERENCE

This application is a continuation-in-part of application Ser. No. 08/810,825 filed Mar. 6, 1997 entitled DISTAL PROTECTION DEVICE, and assigned to the same assignee as the present invention, now U.S. Pat. No. 5,814,064.

The following co-pending patent application is hereby incorporated by reference U.S. patent application Ser. No. 08/813,794, entitled DISTAL PROTECTION DEVICE which was filed on Mar. 6, 1997, now U.S. Pat. No. 5,827,324 and assigned to the same assignee as the present application.

BACKGROUND OF THE INVENTION

The present invention deals with an emboli capturing system. More specifically, the present invention deals with an emboli capturing system and method for capturing embolic material in a blood vessel during an atherectomy or thrombectomy procedure.

Blood vessels can become occluded (blocked) or stenotic (narrowed) in one of a number of ways. For instance, a stenosis may be formed by an atheroma which is typically a harder, calcified substance which forms on the lumen walls of the blood vessel. Also, the stenosis can be formed of a thrombus material which is typically much softer than an atheroma, but can nonetheless cause restricted blood flow in the lumen of the blood vessel. Thrombus formation can be particularly problematic in a saphenous vein graft (SVG).

Two different procedures have developed to treat a stenotic lesion (stenosis) in vasculature. The first is to deform the stenosis to reduce the restriction within the lumen of the blood vessel. This type of deformation (or dilatation) is typically performed using balloon angioplasty.

Another method of treating stenotic vasculature is to attempt to completely remove either the entire stenosis, or enough of the stenosis to relieve the restriction in the blood vessel. Removal of the stenotic lesion has been done through the use of radio frequency (RF) signals transmitted via conductors, and through the use of lasers, both of which treatments are meant to ablate (i.e., super heat and vaporize) the stenosis. Removal of the stenosis has also been accomplished using thrombectomy or atherectomy. During thrombectomy and atherectomy, the stenosis is mechanically cut or abraded away from the vessel.

Certain problems are encountered during thrombectomy and atherectomy. The stenotic debris which is separated from the stenosis is free to flow within the lumen of the vessel. If the debris flows distally, it can occlude distal vasculature and cause significant problems. If it flows proximally, it can enter the circulatory system and form a clot in the neural vasculature, or in the lungs, both of which are highly undesirable.

Prior attempts to deal with the debris or fragments have included cutting the debris into such small pieces (having a size on the order of a blood cell) that they will not occlude vessels within the vasculature. However, this technique has certain problems. For instance, it is difficult to control the size of the fragments of the stenotic lesion which are severed. Therefore, larger fragments can be severed accidentally. Also, since thrombus is much softer than an atheroma, it tends to break up easier when mechanically engaged by a cutting instrument. Therefore, at the moment that the thrombus is mechanically engaged, there is a danger that it can be dislodged in large fragments which would occlude the vasculature.

Another attempt to deal with debris severed from a stenosis is to remove the debris, as it is severed, using suction. However, it may be necessary to pull quite a high vacuum in order to remove all of the pieces severed from the stenosis. If a high enough vacuum is not used, all of the severed pieces will not be removed. Further, when a high vacuum is used, this can tend to cause the vasculature to collapse.

A final technique for dealing with the fragments of the stenosis which are severed during atherectomy is to place a device distal to the stenosis during atherectomy to catch the pieces of the stenosis as they are severed, and to remove those pieces along with the capturing device when the atherectomy procedure is complete. Such capture devices have included expandable filters which are placed distal of the stenosis to capture stenosis fragments. Problems are also associated with this technique. For example, delivery of such devices in a low profile, predeployment configuration can be difficult. Further, some devices include complex and cumbersome actuation mechanisms. Also, retrieving such capture devices, after they have captured emboli, can be difficult as well.

SUMMARY OF THE INVENTION

An emboli capturing system captures emboli in a body lumen. A first elongate member has a proximal end and a distal end. An expandable emboli capturing device is mounted proximate the distal end of the first elongate member, and is movable between a radially expanded position and a radially contracted position. When in the expanded position, the emboli capturing device forms a basket with a proximally opening mouth. A second elongate member has a proximal and a distal end with a lumen extending therebetween. The lumen is sized to slidably receive a portion of the first elongate member. An expandable delivery device is mounted to the distal end of the second elongate member and is movable from a radially retracted position to a radially expanded position. The delivery device has a receiving end configured to receive the emboli capturing device, and retains at least the mouth of the emboli capturing device in a radially retracted position.

BRIEF DESCRIPTION OF THE DRAWINGS

FIG. 1 shows a distal protection device of the present invention in a deployed position.

FIG. 2 shows the distal protection device shown in FIG. 1 in a collapsed position.

FIG. 3 shows an end view of a portion of the distal protection device shown in FIGS. 1 and 2.

FIG. 4 shows a cross-sectional view of a portion of the distal protection device shown in FIGS. 1–3 in the deployed position.

FIG. 5 shows a second embodiment of the distal protection device according to the present invention in a deployed position.

FIG. 6 shows an end view of the distal protection device shown in FIG. 5.

FIG. 7 shows a cross-sectional view of the distal protection device shown in FIGS. 5 and 6 in the collapsed position.

FIG. 8 shows a third embodiment of a distal protection device according to the present invention in a deployed position.

FIG. 9 is a side sectional view of an alternate embodiment illustrating how the expandable members of the present invention are attached to a guidewire.

FIG. 10 is a sectional view taken along section lines 10—10 in FIG. 9.

FIGS. 11A and 11B show a fourth and fifth embodiment, respectively, of a distal protection device according to the present invention in a deployed position.

FIG. 12 illustrates the operation of a distal protection device in accordance with the present invention.

FIGS. 13A–17B show additional embodiments of distal protection devices which expand and collapse based on movement of a mechanical actuator.

FIGS. 21A–21C illustrate another embodiment in accordance with the present invention in which the protection device is formed with a shape memory alloy frame and an attached filter or mesh mounted to the frame.

FIGS. 22A–22C illustrate another embodiment in accordance with the present invention in which the distal protection devices shown in FIGS. 21A–21C are delivered and deployed.

FIGS. 23A–23E illustrate another embodiment in accordance with the present invention in which the distal protection devices shown in FIGS. 21A–21C are retrieved.

FIGS. 24A–24C illustrate another embodiment in accordance with the present invention in which the distal protection devices shown in FIGS. 21A–21C are retrieved.

DETAILED DESCRIPTION OF THE PREFERRED EMBODIMENTS

Figure 14A:
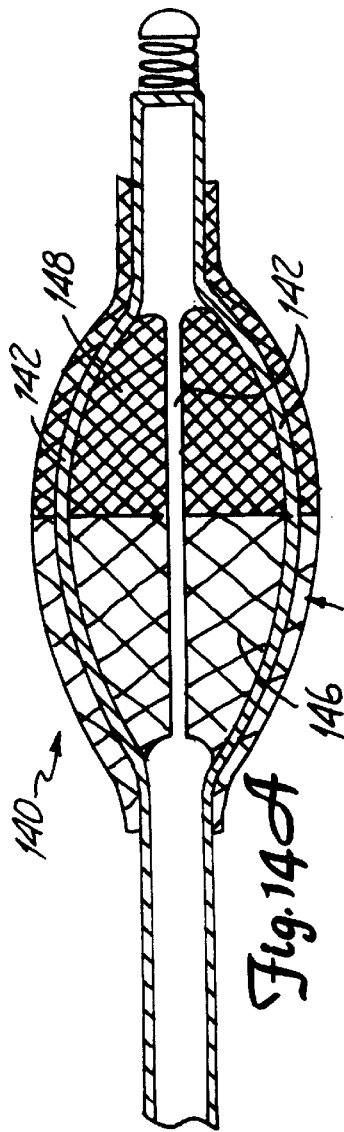

FIG. 1 illustrates protection device 10 in a deployed position within the lumen of a blood vessel 12. Protection device 10 preferably includes hollow guidewire 14 (or a hypotube having the same general dimensions as a guidewire) having a coil tip 16, and a capturing assembly 18. Capturing assembly 18, in the embodiment shown in FIG. 1, includes an inflatable and expandable member 20 and mesh 22.

An interior of expandable member 20 is preferably coupled for fluid communication with an inner lumen of guidewire 14 at a distal region of guidewire 14. When deployed, inflatable member 20 inflates and expands to the position shown in FIG. 1 such that capturing assembly 18 has an outer periphery which approximates the inner periphery of lumen 12.

Mesh 22 is preferably formed of woven or braided fibers or wires, or a microporous membrane, or other suitable filtering or netting-type material. In one preferred embodiment, mesh 22 is a microporous membrane having holes therein with a diameter of approximately 100 μm. Mesh 22 can be disposed relative to inflatable member 20 in a number of different ways. For example, mesh 22 can be formed of a single generally cone-shaped piece which is secured to the outer or inner periphery of inflatable member 20. Alternatively, mesh 22 can be formed as a spiral strip which is secured about the outer or inner periphery of inflatable member 20 filling the gaps between the loops of inflatable member 20. Alternatively, mesh 22 can be formed of a number of discrete pieces which are assembled onto inflatable member 20.

Hollow guidewire 14 preferably has a valve 24 coupled in a proximal portion thereof. During operation, a syringe is preferably connected to the proximal end of guidewire 14, which preferably includes a fluid hypotube. The syringe is used to pressurize the fluid such that fluid is introduced through the lumen of hollow guidewire 14, through valve 24, and into inflatable member 20. Upon being inflated, inflatable member 20 expands radially outwardly from the outer surface of guidewire 14 and carries mesh 22 into the deployed position shown in FIG. 1. In this way, capturing assembly, or filter assembly, 18 is deployed distally of stenosis 26 so that stenosis 26 can be severed and fragmented, and so the fragments from stenosis 26 are carried by blood flow (indicated by arrow 28) into the basket or chamber formed by the deployed filter assembly 18. Filter assembly 18 is then collapsed and removed from vessel 12 with the fragments of stenosis 26 contained therein.

FIG. 2 illustrates protection device 10 with filter assembly 18 in the collapsed position. Similar items to those shown in FIG. 1 are similarly numbered. FIG. 2 illustrates that mesh 22 is easily collapsible with inflatable member 20. In order to collapse filter assembly 18, fluid is preferably removed from inflatable member 20 through the lumen of hollow guidewire 14 and through two-way valve 24. This can be done using the syringe to pull a vacuum, or using any other type of suitable fluid removal system.

Inflatable member 20 is preferably formed of a material having some shape memory. Thus, when inflatable member 20 is collapsed, it collapses to approximate the outer diameter of hollow guidewire 14. In one preferred embodiment, inflatable member 20 is formed of a resilient, shape memory material such that it is inflated by introducing fluid under pressure through the lumen in hollow guidewire 14 into inflatable member 20. When pressure is released from the lumen in hollow guidewire 14, inflatable member 20 is allowed to force fluid out from the interior thereof through two-way valve 24 and to resume its initial collapsed position. Again, this results in filter assembly 18 assuming its collapsed position illustrated in FIG. 2.

FIG. 3 illustrates a view taken from the distal end of device 10 with mesh 22 removed for clarity. FIG. 3 shows that, when inflatable member 20 is deployed outwardly, mesh 22 (when deployed between the loops of inflatable member 20) forms a substantially lumen-filling filter which allows blood to flow therethrough, but which provides a mechanism for receiving and retaining stenosis fragments carried into mesh 22 by blood flow through the vessel.

FIG. 3 also shows that inflatable member 20 preferably has a proximal end portion 29 which is connected to the outer periphery of guidewire 14. Although end 29 need not be connected to guidewire 14, it is preferably connected using adhesive or any other suitable connection mechanism. By fixedly connecting proximal end portion 29 to guidewire 14, this increases the stability of the filter assembly 18 upon deployment.

FIG. 4 is a cross-sectional view of a portion of protection device 10. FIG. 4 shows protection device 10 with filter assembly 18 in the expanded or deployed position. FIG. 4 also better illustrates that guidewire 14 is hollow and has a longitudinal lumen 30 extending therethrough. Longitudinal lumen 30 is connected in fluid communication with an interior of inflatable member 20 through aperture 32 which is provided in the wall of guidewire 14. FIG. 4 also shows that, in one preferred embodiment, a core wire 34 extends through lumen 30 from a proximal end thereof where it is preferably brazed to a portion of a hypotube which may be connected to the proximal portion of guidewire 14. The core wire 34 extends to the distal end of guidewire 14 where it is connected to coil tip 16. In one preferred embodiment, coil tip 16 is brazed or otherwise welded or suitably connected to the distal portion of core wire 34.

FIG. 4 further shows that, in the preferred embodiment, inflatable member 20 inflates to a generally helical, conical shape to form a basket opening toward the proximal end of guidewire 14. FIG. 4 further illustrates, in the preferred embodiment, mesh 22 has a distal portion 38 which is connected to the exterior surface of guidewire 14, at a distal region thereof, through adhesive 36 or any other suitable connection mechanism.

FIG. 5 illustrates a second embodiment of a distal protection device 40 in accordance with the present invention. Device 40 includes hollow guidewire 42, filter assembly 44 and coil tip 16. Filter assembly 44 includes a plurality of inflatable struts 46 and mesh 47. Each strut 46 has a distal end 48 and proximal end 50. Inflatable struts 46 also have an interior which is coupled in fluid communication, through distal end 48 thereof, with the lumen in hollow guidewire 42. Struts 46 are preferably configured such that, upon being inflated, the proximal ends 50 deploy radially outwardly away from the outer surface of hollow guidewire 42 to assume a dimension which approximates the inner dimension of lumen 58 in which they are inserted.

Mesh 47, as with mesh 22 shown in FIG. 1, is deployed either on the outer or inner surface of inflatable struts 46, such that, when the inflatable struts 46 are deployed radially outwardly, mesh 47 forms a generally conical basket opening toward the proximal end of hollow guidewire 42. As with the embodiment shown in FIG. 1, mesh 47 can be applied to either the outer or the inner surface of struts 46. It can be applied to struts 46 as one unitary conical piece which is adhered about distal ends 48 of struts 46 using adhesive (or about the distal end of guidewire 42 using adhesive) and secured to the surface of the struts 46 also using adhesive. Alternatively, mesh 47 can be applied to struts 46 in a plurality of pieces which are individually or simultaneously secured to, and extend between, struts 46.

FIG. 6 is an end view of distal protection device 40 shown in FIG. 5 taken from the distal end of distal protection device 40. When struts 46 are deployed outwardly, mesh 47 forms a substantially lumen-filling filter which allows blood to flow therethrough, but which provides a mechanism for receiving and retaining stenosis fragments from stenosis 56 carried into mesh 47 by blood flow through the vessel.

FIG. 7 is a cross-sectional view of a portion of distal protection device 40 shown in FIGS. 5 and 6. FIG. 7 shows filter assembly 44 in the collapsed position in which it approximates the outer diameter of guidewire 42. FIG. 7 also shows that, in the preferred embodiment, the distal ends 48 of struts 46 are in fluid communication with an inner lumen 52 in hollow guidewire 42 through apertures 54 in the wall of guidewire 42.

FIG. 8 illustrates another embodiment of a distal protection device 60 in accordance with the present invention. Distal protection device 60 is similar to those shown in other figures, and similar items are similarly numbered. However, distal protection device 60 includes hollow guidewire 63 which has a lumen in fluid communication with an interior of a pair of inflatable struts 62. Inflatable struts 62 have an inner surface 64 which is generally concave, or hemispherical, or otherwise appropriately shaped such that it extends about a portion of the outer surface of hollow guidewire 63. Mesh portions 66 extend between the inflatable struts 62 so that inflatable struts 62 and mesh portions 66, when deployed outwardly as shown in FIG. 8, form a basket shape which opens toward the proximal end of hollow guidewire 63.

FIG. 9 illustrates another system for attaching inflatable struts to a hollow guidewire for a distal protection device 70 in accordance with the present invention. Distal protection device 70 is similar to the distal protection devices shown in the previous figures in that a plurality of inflatable struts 72 are provided and preferably have a mesh portion extending therebetween. For the sake of clarity, the mesh portion is eliminated from FIG. 9. However, it will be understood that, when deployed, distal protection device 70 forms a generally basket-shaped filter assembly which opens toward the proximal end of hollow guidewire 74.

In the embodiment shown in FIG. 9, hollow guidewire 74 has a distal end 75 which is open. An endcap 76 is disposed about the distal end 75 of hollow guidewire 74 and defines an internal chamber or passageway 78. Endcap 76 has a proximal end 80 which has openings therein for receiving the ends of inflatable struts 72. Thus, in order to inflate inflatable struts 72, the operator pressurizes fluid within the lumen of hollow guidewire 74 forcing fluid out through distal end 75 of hollow guidewire 74, through passageway 78, and into inflatable struts 72. In order to collapse distal protection device 70, the operator draws a vacuum which pulls the fluid back out of inflatable struts 72, through passageway 78 and, if necessary, into the lumen of hollow guidewire 74.

FIG. 10 is an end view of endcap 76 taken along lines 10—10 in FIG. 9. FIG. 10 shows that proximal end 80 of endcap 76 preferably includes a first generally central aperture 82 for receiving the distal end of hollow guidewire 74. Aperture 82 is sized just larger than, or approximating, the outer diameter of hollow guidewire 74 such that it fits snugly over the distal end 75 of hollow guidewire 74. Endcap 76 is then fixedly connected to the distal end 75 of hollow guidewire 74 through a friction fit, a suitable adhesive, welding, brazing, or another suitable connection technique.

FIG. 10 also shows that proximal end 80 of endcap 76 includes a plurality of apertures 84 which are spaced from one another about end 80. Apertures 84 are sized to receive open ends of inflatable struts 72. In the preferred embodiment, inflatable struts 72 are secured within apertures 84 using a suitable adhesive, or another suitable connection technique. Also, in the preferred embodiment, spring tip 16 is embedded in, or otherwise suitably connected to, endcap 76.

FIGS. 11A and 11B show two other preferred embodiments of a distal protection device in accordance with the present invention. FIG. 11A shows distal protection device 90 which includes hollow guidewire 92 having a lumen running therethrough, inflatable member 94 and mesh portion 96. FIG. 11A shows that inflatable member 94, when inflated, forms a ring about the outer surface of hollow guidewire 92. The ring has an inner periphery 98 which is spaced from the outer surface of hollow guidewire 92 substantially about the entire radial periphery of hollow guidewire 92. Mesh portion 96 extends between the outer surface of hollow guide 92 and the inner periphery 98 of inflatable member 94. Thus, a substantially disc-shaped filter assembly is provided upon deployment of distal protection device 90. As with the other embodiments, deployment of distal protection device 90 is accomplished by providing fluid through the inner lumen of hollow guidewire 92 into an interior of inflatable member 94 which is in fluid communication with the inner lumen of hollow guidewire 92.

In one preferred embodiment, end 100 of inflatable member 94 is coupled to a coupling portion 102 of inflatable member 94 such that stability is added to inflatable member 94, when it is inflated.

FIG. 11B illustrates another distal protection device 104 which includes a hollow guidewire 106 and an inflatable member 108. Device 104 is similar to distal protection device 90 except that, rather than having only a single inflatable ring upon deployment of distal protection device 104, a plurality of generally equal-diameter rings are formed into a helix shape. In the preferred embodiment, distal protection device 104 includes a mesh sleeve 110 which extends about the outer or inner surface of the helix formed by inflatable member 108. In one embodiment, mesh sleeve 110 is connected to the outer surface of hollow guidewire 106 in a region 112 proximate, but distal of, inflatable member 108. In another preferred embodiment, the proximal end of mesh sleeve 110 is connected to the outer perimeter of inflatable member 108. Thus, distal protection device 104 forms a generally basket-shaped filter assembly which opens toward a proximal end of guidewire 106.

As with the other embodiments, both distal protection device 90 shown in FIG. 11A and distal protection device 104 shown in FIG. 11B are preferably collapsible. Therefore, when collapsed, the distal protection devices 90 and 104 preferably have an outer dimension which approximates the outer dimension of hollow guidewires 92 and 106, respectively. Further, as with the other embodiments, distal protection devices 90 and 104 can either be biased in the deployed or collapsed positions, and deployment and collapse can be obtained either by pulling a vacuum, or pressurizing the fluid within the lumen of the hollow guidewires 92 and 106.

FIG. 12 illustrates the use of a distal protection device in accordance with the present invention. For the sake of clarity, the present description proceeds with respect to distal protection device 10 only. Device 10 is shown filtering stenosis fragments from the blood flowing through the lumen of vessel 12. FIG. 12 also shows a dilatation device 120 which can be any suitable dilatation device for dilating, cutting, fragmenting, or abrading, portions of stenosis 26. In the preferred embodiment, device 120 is used in an over-the-wire fashion over hollow guidewire 14. Thus, filter assembly 18 is first advanced (using guidewire 14) distal of stenosis 26. Then, filter assembly 18 is deployed outwardly to the expanded position. Dilatation device 120 is then advanced over guidewire 14 to stenosis 26 and is used to fragment or abrade stenosis 26. The fragments are received within the basket of filter assembly 18. Filter assembly 18 is then collapsed, and filter assembly 18 and dilatation device 120 are removed from vessel 12. Alternatively, dilatation device 120 can be removed first and filter assembly 18 is then removed along with guidewire 14.

It should be noted that the stenosis removal device (or atherectomy catheter) 120 used to fragment stenosis 26 can be advanced over guidewire 14. Therefore, the device according to the present invention is dual functioning in that it captures emboli and serves as a guidewire. The present invention does not require adding an additional device to the procedure. Instead, the present invention simply replaces a conventional guidewire with a multi-functional device.

FIGS. 13A–17B illustrate embodiments of various distal protection devices wherein deployment and contraction of the distal protection device is accomplished through a mechanical push/pull arrangement.

FIGS. 13A and 13B illustrate a distal protection device 122. FIG. 13A shows device 122 in an undeployed position and FIG. 13B shows device 122 in a deployed position. Distal protection device 122 includes a slotted Nitinol tube 124 which has a lumen 126 extending therethrough. Tube 124 has a plurality of slots 128 at a distal region thereof. The distal portion of slots 128 are covered by mesh 130 which, in the preferred embodiment, is a flexible microporous membrane. Device 122 also preferably includes a mandrel 132 which extends through the inner lumen 126 of tube 124 and is attached to the distal end of tube 124. In the preferred embodiment, mandrel 132 is attached to the distal end of tube 124 by an appropriate adhesive, brazing, welding, or another suitable connection technique. Tube 124 also has, on its inner periphery in a proximal region thereof, a plurality of locking protrusions 134. Lock protrusions 134 are preferably arranged about a proximal expandable region 136 disposed on mandrel 132.

In order to deploy device 122 into the deployed position shown in FIG. 13B, the operator preferably first advances tube 124 distally of the lesion to be fragmented. In the preferred embodiment, tube 124 has a size on the order of a guidewire, such as a 0.014 inch outer diameter. Therefore, it easily advances beyond the stenosis to be fragmented. The operator then pushes on the proximal region of tube 124 and pulls on the proximal end of mandrel 132. This causes two things to happen. First, this causes the struts formed by slots 128 to expand radially outwardly, and carry with them, microporous membrane 130. Thus, microporous membrane 130 forms a generally basket-shaped filter assembly which opens toward the proximal end of tube 124. In addition, proximal expandable member 136 expands and engages protrusions 134. This locks device 122 in the deployed and expanded position. In order to move the device 122 to the collapsed position, the physician simply pushes on mandrel 132 and pulls on the proximal end of tube 124. This causes device 122 to return to the undeployed position shown in FIG. 13A.

It should be noted that device 122 can optionally be provided with a stainless steel proximal hypotube attachment. Also, the struts defined by slots 128 can be expanded and retracted using a fluid coupling instead of a mandrel. In other words, the proximal end of tube 124 can be coupled to a pressurizable fluid source. By making slots 128 very thin, and pressurizing the fluid, the struts expand outwardly. Further, by pulling vacuum on the pressurizable fluid, the struts collapse.

FIG. 14A illustrates distal protection device 140 which is similar to that shown in FIGS. 13A and 13B, except that the struts 142 are formed of a metal or polymer material and are completely covered by mesh 144. Mesh 144 includes two mesh portions, 146 and 148. Mesh portion 146 is proximal of mesh portion 148 on device 140 and is a relatively loose mesh which will allow stenosis fragments to pass therethrough. By contrast, mesh 148 is a fairly tight mesh, or a microporous membrane, (or simply loose mesh portion 146 with a microporous membrane or other suitable filter material bonded or cast or otherwise disposed thereover) which does not allow the fragments to pass therethrough and therefore captures and retains the fragments therein. The mesh portions can provide a memory set which, in the relaxed position, is either deployed or collapsed.

Figure 14B:
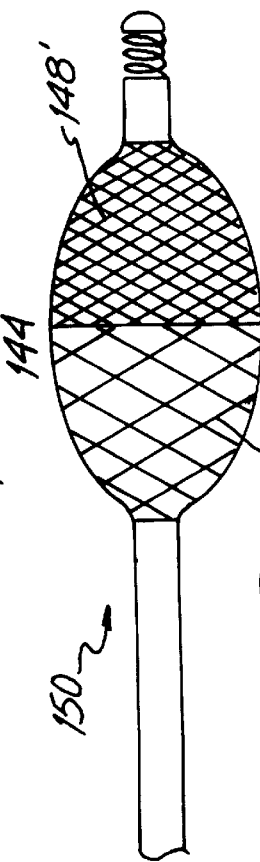

FIG. 14B illustrates a device 150 which is similar to device 140 shown in FIG. 14A, except struts 142 are eliminated and the two mesh portions 146' and 148' are simply joined together at a region 152. Also, the two mesh portions 146' and 148' are not two different discrete mesh portions but are formed of the same braided mesh material wherein the braid simply has a different pitch. The wider pitch in region 146' provides a looser mesh, whereas the narrower pitch in region 148' provides a tighter mesh that traps the embolic material.

Figure 14C:
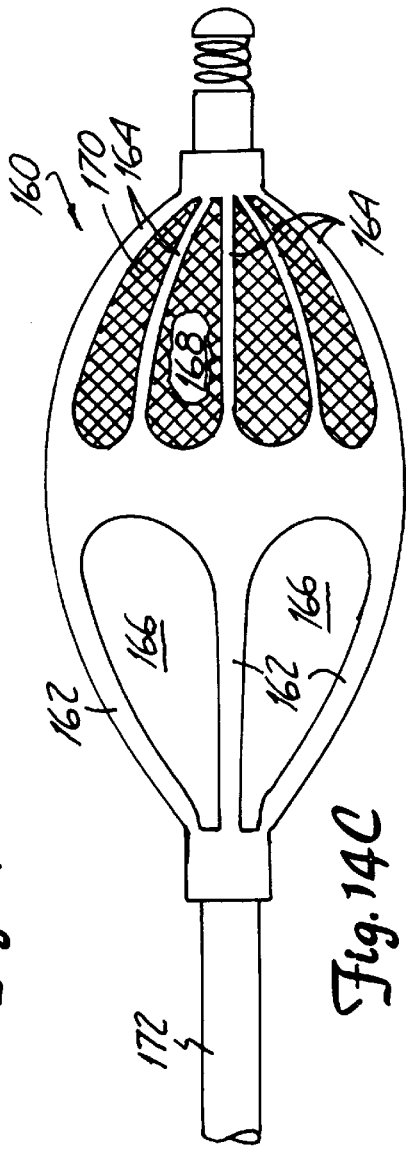

FIG. 14C illustrates a distal protection device 160 which is similar to that shown in FIG. 14A. However, rather than simply providing a slotted tube, distal protection device 160 includes a plurality of struts 162 on a proximal region thereof and a plurality of struts 164 on the distal region thereof. Struts 162 are spaced further apart than struts 164 about the periphery of protection device 160. Therefore, struts 162 define openings 166 which are larger than the openings 168 defined by struts 164 and allow stenosis fragments to pass therethrough. Also, struts 164 have secured to the interior surface thereof a filter or mesh portion 170. When deployed, filter portion 170 forms a substantially basket-shaped filter device opening toward the proximal region of tube 172.

FIG. 15 illustrates the operation of another distal protection device 176. Distal protection device 176 includes a tube 178 and a push/pull wire 180. Tube 178 has, at the distal end thereof, a filter assembly 182. Filter assembly 182 includes a plurality of preferably metal struts 184 which have a microporous membrane, or other suitable mesh 186 disposed thereon. Tube 178 also preferably includes end cap 188 and umbrella-like expansion structure 190 disposed at a distal region thereof. Expansion structure 190 is connected to the distal region of tube 178 and to metal struts 184 such that, when push/pull wire 180 is pulled relative to tube 178, expansion member 190 exerts a radial, outwardly directed force on struts 184 causing them to expand radially outwardly relative to the outer surface of tube 178. This causes microporous membrane or mesh 186 to be deployed in a manner opening toward the proximal end of tube 178 to catch embolic material. Struts 184 can also be formed of an appropriate polymer material.

FIGS. 16A and 16B illustrate a protection device in accordance with another embodiment of the present invention. FIG. 16A illustrates distal protection device 192. Device 192 includes guidewire 194, actuator wire 19G, and filter assembly 198. Filter assembly 198 includes an expandable ring 200, such as an expandable polymer or metal or other elastic material, which has attached thereto mesh 202. Mesh 202 is also attached to guidewire 194 distally of ring 200. Actuator wire 196 is attached to sleeve or sheath 204 which is positioned to fit about the outer periphery of expandable ring 200, when expandable ring 200 is in the collapsed position.

Thus, when sheath 204 is moved distally of expandable ring 200, expandable ring 200 has shape memory which causes it to expand into the position shown in FIG. 16A. Alternatively, when sheath 204 is pulled proximally by pulling actuator wire 196 relative to guidewire 194, sheath 204 collapses ring 200 and holds ring 200 in the collapsed position within sheath 204. Manipulating wires 194 and 196 relative to one another causes device 192 to move from the deployed position to the collapsed position, and vice versa.

FIG. 16B is similar to device 192 except that, instead of having an expandable ring 200 connected at one point to wire 194, distal protection device 206 includes expandable member 208 which is formed of an elastic coil section of wire 194. Thus, elastic coil section 208 has a shape memory which causes it to expand into the generally helical, conical shape shown in FIG. 16B. However, when sheath 204 is pulled proximally relative to expandable member 208, this causes sheath 204 to capture and retain expandable member 208 in a collapsed position. When sheath 204 is again moved distally of expandable member 208, expandable member 208 returns to its expanded position shown in FIG. 16B carrying with it mesh 210 into a deployed position. In the preferred embodiment, sheath 204 is formed of a suitable polymer material and expandable member 208 and expandable ring 200 are preferably formed of Nitinol.

FIGS. 17A and 17B illustrate the operation of another distal protection device 212. Protection device 212 includes guidewire 214 and filter assembly 216. In the preferred embodiment, filter assembly 216 includes a wire braid portion 218 which extends from a distal region of guidewire 214 proximally thereof. Braid portion 218 is formed of braided filaments or fibers which have a shape memory causing them to form a deployed, basket-shaped filter, such as that shown in FIG. 17A, in the unbiased position. Braided portion 218 terminates at its proximal end in a plurality of eyelets 220. One or more cinch wires 222 are preferably threaded through eyelets 220. By pushing on guidewire 214 and pulling on cinch wires 222, the operator is able to cinch closed, and pull proximally, the proximal portion of mesh 218. This causes mesh 218 to collapse tightly about the outer surface of wire 214.

Therefore, during operation, the operator holds mesh 218 in the collapsed position and inserts protection device 212 distally of the desired stenosis. The operator then allows cinch wire 222 to move distally relative to guidewire 214. This allows mesh 218 to open to the deployed position shown in FIG. 17A which has an outer diameter that approximates the inner diameter of the lumen within which it is disposed. Filter assembly 216 is then disposed to capture embolic material from blood flowing therethrough. Once the embolic material is captured, the operator again moves cinch wire 222 proximally relative to guidewire 214 to collapse filter assembly 216 and capture and retain the embolic material in filter assembly 216. The device 212 is then removed.

FIG. 17B shows distal protection device 212 except that in the embodiment shown in FIG. 172, protection device 212 is not disposed distally of the stenosis, but rather proximally. This results, for example, in an application where the blood flow is proximal of the stenosis rather than distal. Further, in the embodiment shown in FIG. 17B, guidewire 214 is preferably hollow and the cinch wire 222 extends through the lumen therein. By pushing on guidewire 214, a force is exerted on mesh 218 in the distal direction. This causes cinch wire 222 to tightly close the distal opening in filter assembly 216 and to collapse mesh portion 218. By contrast, by allowing cinch wire 222 to move distal relative to hollow guidewire 214, mesh portion 218 expands and filter assembly 216 is deployed as shown in FIG. 17B.

Figure 18A:
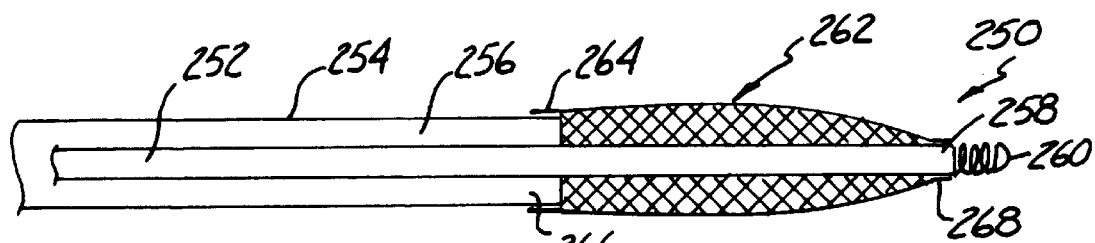
FIGS. 18A–18D illustrate an additional embodiment of a distal protection device which is deployed and collapsed using a rolling flap configuration.
Figure 18B:
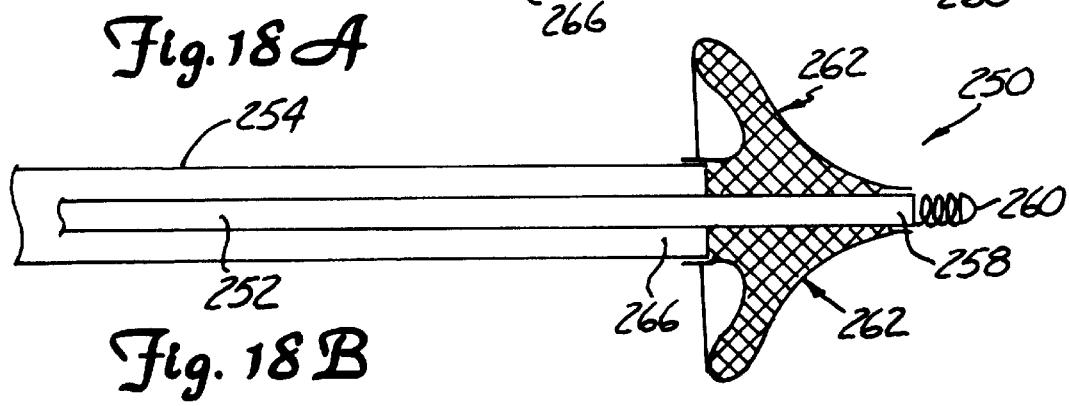

FIGS. 18A and 18B illustrate a distal protection device 250 in accordance with another aspect of the present invention. Device 250 includes inner wire 252 and outer tube 254. In the preferred embodiment, inner wire 252 is a core wire and outer tube 254 has a lumen 256 therein large enough to accommodate longitudinal movement of inner wire 252 therein. Also, in the preferred embodiment, inner wire 252 has, coupled to its distal end 258, a spring tip 260.

Device 250 includes expandable mesh or braid portion 262. Expandable portion 262 has a proximal end 264 which is attached to the distal end 266 of tube 254. Also, expandable member 262 has a distal end 268 which is attached to the distal end 258 of inner wire 252.

Expandable member 262 is preferably a mesh or braided material which is coated with polyurethane. In one preferred embodiment, a distal portion of expandable member 262 has a tighter mesh than a proximal portion thereof, or has a microporous membrane or other suitable filtering mechanism disposed thereover. In another preferred embodiment, expandable member 262 is simply formed of a tighter mesh or braided material which, itself, forms the filter. FIG. 18A illustrates device 250 in a collapsed, or insertion position wherein the outer diameter of mesh portion 262 closely approximates the outer diameters of either inner wire 252 or outer tube 254.

FIG. 18B illustrates device 250 in the deployed position in which expandable member 262 is radially expanded relative to the collapsed position shown in FIG. 18A. In order to deploy device 250, the outer tube 254 is moved distally with respect to inner wire 252 such that the distal ends 266 and 258 of wires 254 and 252 move longitudinally toward one another. Relative movement of ends 266 and 258 toward one another causes the mesh of expandable member 262 to buckle and fold radially outwardly. Thus, the outer diameter of expandable member 262 in the deployed position shown in FIG. 18B closely approximates the inner diameter of a vessel within which it is deployed.

Figure 18C:
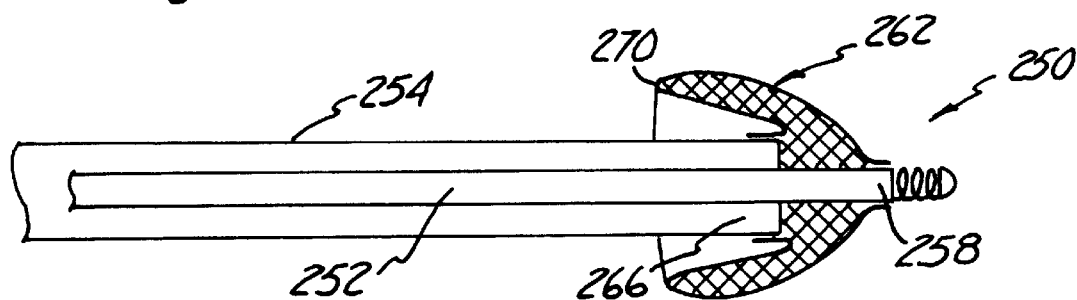

FIG. 18C illustrates device 250 in a partially collapsed position. In FIG. 18C, the distal end 266 of outer tube 254 and the distal end 258 of inner wire 252 are moved even closer together than they are as shown in FIG. 18B. This causes expandable mesh portion 262 to fold over itself and form a rolling, proximally directed flap 270. As longitudinal movement of inner wire 252 proximally with respect to outer tube 254 continues, mesh portion 262 continues to fold over itself such that the rolling flap portion 270 has an outer radial diameter which continues to decrease. In other words, expandable mesh portion 262 continues to fold over itself and to collapse over the outer periphery of outer tube 254.

Figure 18D:
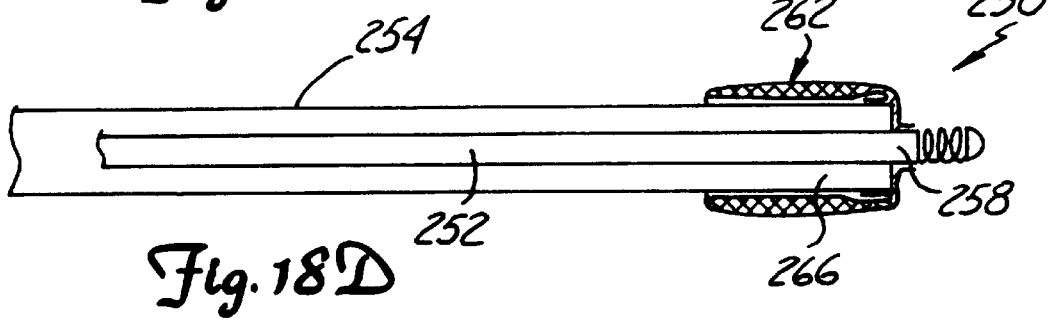

FIG. 18D illustrates device 250 in a fully collapsed position in which it retains emboli captured therein. In FIG. 18D, the distal end 266 of outer tube 254 has been advanced as far distally as it can relative to the distal end 258 of inner wire 252. This causes expandable mesh portion 262 to fold all the way over on itself such that it lies against, and closely approximates the outer diameter of, outer tube 254. Device 250 thus captures any emboli filtered from the vessel within which it was deployed, and can be removed while retaining that embolic material.

Figure 19:
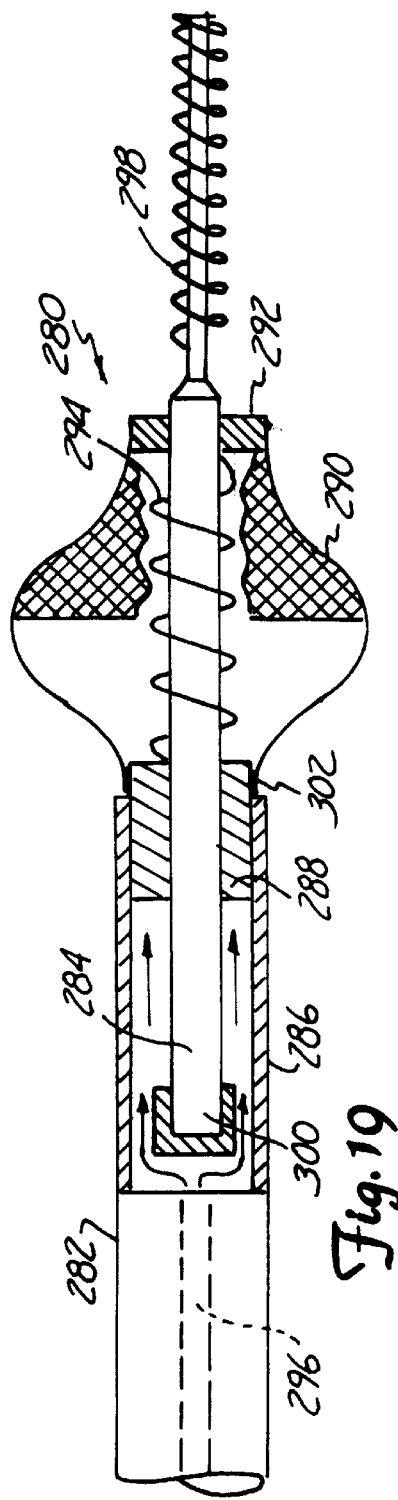
FIG. 19 illustrates another embodiment in accordance with the present invention in which the protection device is deployed using fluid pressure and a movable collar.

FIG. 19 illustrates device 280 which depicts a further aspect in accordance with the present invention. Device 280 includes outer tube 282, core wire 284, transition tube 286, movable plunger 288, expandable member 290, fixed collar 292 and bias member 294.

In the preferred embodiment, tube 282 comprises a proximal hypotube which is coupled to a plunger that selectively provides fluid under pressure through an inflation lumen 296. Inner wire 284 is preferably a tapered core wire which terminates at its distal end in a spring coil tip 298 and which is coupled at its proximal end 300 to transition tube 286. Transition tube 286 is preferably an outer polymer sleeve either over hypotube 282, or simply disposed by itself and coupled to a hypotube 282. Transition tube 286 is capable of withstanding the inflation pressure provided by the fluid delivered through the inflation lumen 296.

Movable collar 288 is preferably slidably engageable with the interior surface of transition tube 286 and with the exterior surface of core wire 284, and is longitudinally movable relative thereto. Slidable collar 288 has, attached at its distal end, bias spring 294 which is preferably coiled about core wire 284 and extends to fixed collar 292. Fixed collar 292 is preferably fixedly attached to the exterior surface of a distal portion of core wire 284.

Expandable member 290 is preferably formed, at a proximal portion thereof, of either discrete struts, or another suitable frame (such as a loose mesh) which allows blood and embolic material to flow therethrough. The proximal end 302 of expandable member 290 is coupled to a distal region of movable collar 288. The distal portion of expandable member 290 is preferably formed of a filtering material which is suitable for allowing blood flow therethrough, but which will capture embolic material being carried by the blood.

In one preferred embodiment, spring 294 is biased to force collars 288 and 292 away from one another. Thus, as spring 294 urges collars 288 and 292 away from one another, collar 288 retracts within transition tube 286 pulling expandable member 290 into a collapsed position about core wire 284. However, in order to deploy collapsible member 290 as shown in FIG. 19, the operator preferably actuates a plunger (not shown) which delivers pressurized fluid through lumen 296. The pressurized fluid enters transition tube 286 and travels about the outer periphery of inner core wire 284, thus forcing movable collar 288 to move distally along core wire 284. This overcomes the spring force exerted by spring 294 thus causing collars 288 and 292 to move toward one another, relatively. This motion causes expandable member 290 to buckle and expand outwardly to the deployed position shown in FIG. 19.

Expandable member 290 is collapsed by releasing the pressure applied through lumen 296 (i.e., by causing the plunger to move proximally). This allows spring 294 to again urge collars 288 and 292 away from one another to collapse expandable member 290. In an alternative embodiment, the frame supporting expandable member 290 is imparted with a memory (such as a heat set, or a thermally responsive material which assumes a memory upon reaching a transition temperature) such that the resting state of the frame supporting expandable member 290 is in a collapsed position. This eliminates the need for spring 294. The expandable member 290, in that preferred embodiment, is expanded using the hydraulic pressure provided by the pressurized fluid introduced through lumen 296, and it is collapsed by simply allowing the memory in expandable member 290 to force fluid from transition tube 286 back through lumen 296.

Figure 20A:
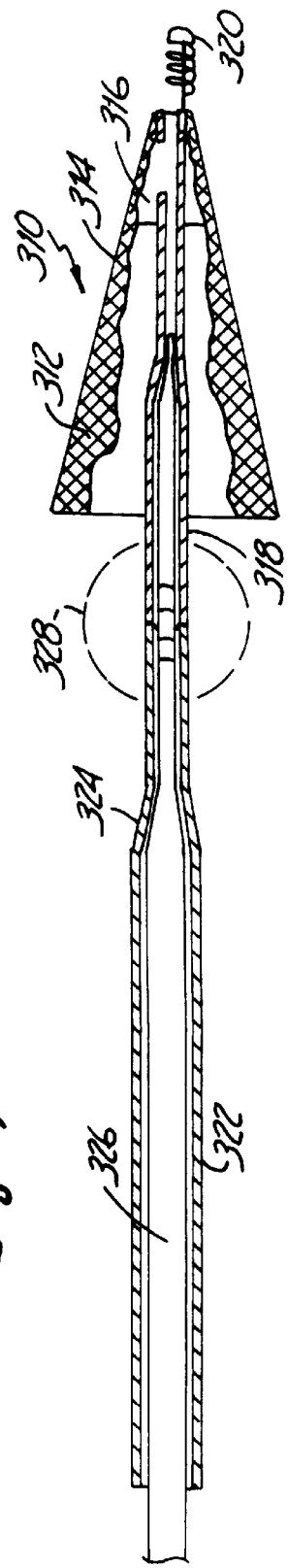
FIGS. 20A and 20B illustrate another aspect of the present invention in which two longitudinally movable members used to deploy the distal protection device are disconnectably locked to one another.
Figure 20B:
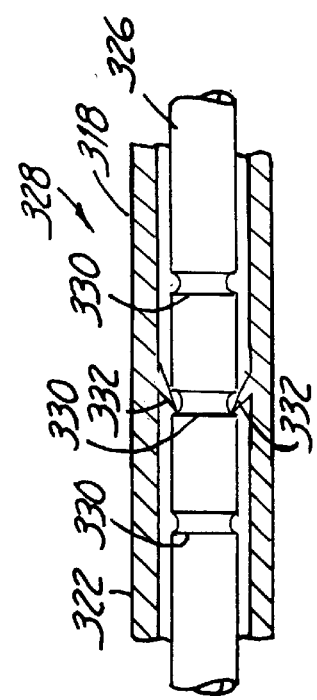

FIGS. 20A and 20B illustrate another aspect in accordance with the present invention. A device 310 includes a mesh portion 312 supported by a frame 314. Expansion of frame 314 to the radially expanded position shown in FIG. 20A is driven by an expandable member, such as a balloon, 316 which is coupled to frame 314. Balloon 316 is coupled to a distal end of a distal hypotube 318, which is formed of a suitable material, such as nitinol. It should be noted that the distal tip of hypotube 318 includes a spring tip 320.

Distal hypotube 318 is shown coupled to a proximal hypotube 322 which has a tapered portion 324 therein. In the preferred embodiment, proximal hypotube 322 is formed of a suitable material, such as stainless steel. A plunger 326 is longitudinally movable within the lumen of both proximal hypotube 322 and distal hypotube 318.

Frame 314, and consequently mesh portion 312, are deployed by the operator moving plunger 326 distally within the lumens of hypotubes 318 and 322. This causes pressurized fluid to enter balloon 316, thereby inflating balloon 316 and driving deployment of frame 314 and mesh 312. In order to collapse frame 314 and mesh 312, the operator preferably moves plunger 326 proximally within the lumens of tubes 318 and 322 to withdraw fluid from within balloon 316. Alternatively, mesh 312 or frame 314 can have a memory set which is either in the inflated or collapsed position such that the operator need only affirmatively move frame 314 and mesh 312 to either the deployed or collapsed position, whichever is opposite of the memory set.

In either case, it is desirable that the operator be able to lock plunger 326 in a single longitudinal position relative to hypotubes 318 and 322. Thus, device 310 includes a locking region 328.

FIG. 20B illustrates locking region 328 in greater detail. FIG. 20B illustrates that, in locking region 328, plunger 326 has a plurality of grooves 330 formed in the outer radial surface thereof. Also, in accordance with the present invention, FIG. 20B illustrates that one of hypotubes 318 or 322 has an inwardly projecting portion 332. In one preferred embodiment, inwardly projecting portion 332 includes an inwardly extending, deflectable, annular rim which extends inwardly from either hypotube 318 or 322. In another preferred embodiment, the inwardly projecting portion 332 includes a plurality of discrete fingers which extend inwardly from one of hypotubes 318 or 322 and which are angularly displaced about the interior periphery of the corresponding hypotube 318 or 322.

In operation, as the operator advances plunger 326 distally within the lumens of hypotubes 318 and 322, inwardly projecting portion 332 rides along the exterior periphery of plunger 326 until it encounters one of grooves 330. Then, inwardly projecting portion 332 snaps into the groove 330 to lock plunger 326 longitudinally relative to tubes 318 and 322.

It should be noted that, in the preferred embodiment, both inwardly projecting portions 332 and grooves 330 are formed such that, when gentle pressure is exerted by the operator on plunger 326 relative to hypotubes 318 and 322, projection portions 332 follow the contour of grooves 330 up and out of grooves 330 so that plunger 326 can again be freely moved within the lumens of hypotubes 318 and 322. Thus, the relative interaction between projecting portions 332 and grooves 330 provides a ratcheting type of operation wherein plunger 326 can be releasably locked into one of a plurality longitudinal positions relative hypotubes 318 and 322, since a plurality of grooves 330 are provided. Plunger 326 can be moved back and forth longitudinally within the lumens of hypotubes 318 and 322 in a ratcheting manner and can be locked into one of a plurality of relative longitudinal positions because there are a plurality of grooves 330 in the exterior of plunger 326. It should also be noted, however, that in another preferred embodiment, a plurality of sets of inwardly projecting portions 332 are provided along the inner longitudinal surface of hypotubes 318 and/or 322. In that case, only a single groove 330 needs to be formed in the exterior surface of plunger 326, and the same type of ratcheting locking operation is obtained.

In the preferred embodiment, at least the exterior of hypotubes 318 and 322, and preferably the exterior of plunger 326, are tapered. This allows device 310 to maintain increased flexibility. It should also be noted that, in the preferred embodiment, hypotubes 318 and 322 are preferably sized as conventional guidewires.

Figure 21A:
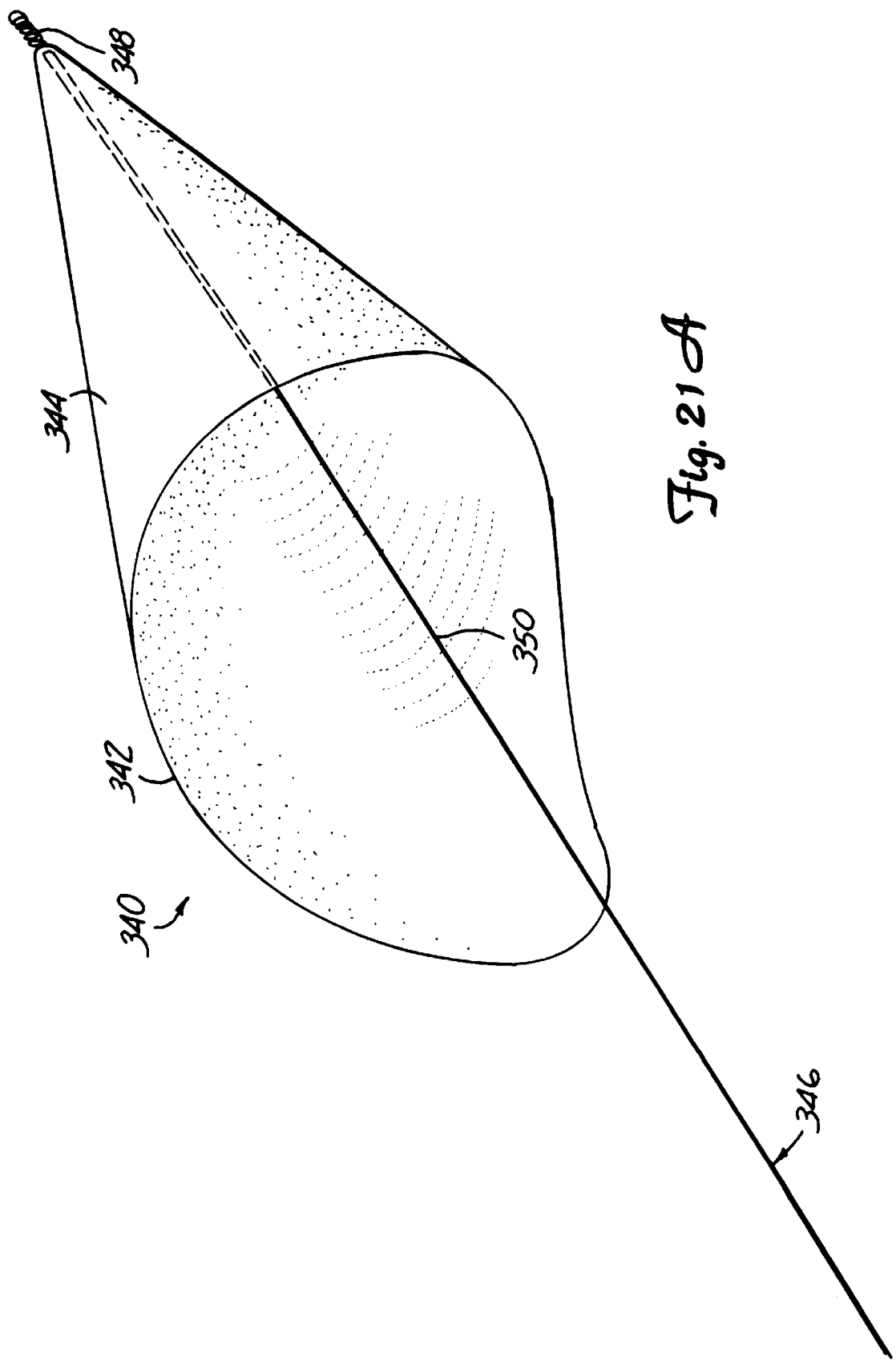

FIG. 21A illustrates a protection device in accordance with another embodiment of the present invention. FIG. 21A illustrates distal protection device 340. Device 340 is similar to devices 192 and 206 shown in FIGS. 16A and 16B. However, in the preferred embodiment, device 340 includes hoop-shaped frame 342, filter portion 344, and wire 346. Hoop-shaped frame 342 is preferably a self-expanding frame formed of a wire which includes a shape memory alloy. In a more preferred embodiment hoop-shaped frame 342 is formed of a nitinol wire having a diameter in a range of approximately 0.002–0.004 inches.

Filter portion 344 is preferably formed of a polyurethane material having holes therein such that blood flow can pass through filter 344, but emboli (of a desired size) cannot pass through filter 344 but are retained therein. In one preferred embodiment, filter material 344 is attached to hoop-shaped frame 342 with a suitable, commercially available adhesive. In another preferred embodiment, filter 344 has a proximal portion thereof folded over hoop-shaped frame 342, and the filter material is attached itself either with adhesive, by stitching, or by another suitable connection mechanism, in order to secure it about hoop-shaped frame 342. This connection is preferably formed by a suitable adhesive or other suitable connection mechanism.

Also, the distal end of filter 344 is preferably attached about the outer periphery of wire 346, proximate coil tip 348 on wire 346.

In one preferred configuration, filter 344 is approximately 15 mm in longitudinal length, and has a diameter at its mouth (defined by hoop-shaped frame 342) of a conventional size (such as 4.0 mm, 4.5 mm, 5 mm, 5.5 mm, or 6 mm). Of course, any other suitable size can be used as well.

Also, in the preferred configuration, filter 344 is formed of a polyurethane material with the holes laser drilled therein. The holes are preferably approximately 100 $\mu$m in diameter. Of course, filter 344 can also be a microporous membrane, a wire or polymer braid or mesh, or any other suitable configuration.

Wire 346 is preferably a conventional stainless-steel guidewire having conventional guidewire dimensions. For instance, in one embodiment, wire 346 is a solid core wire having an outer diameter of approximately 0.014 inches and an overall length of up to 300 cm. Also, in the preferred embodiment, wire 346 has a distal end 350, in a region proximate filter 344, which tapers from an outer diameter at its proximal end which is the same as the outer diameter of the remainder of wire 346, to an outer diameter of approximately 0.055 inches at its distal end. At distal region 350, guidewire 346 is preferably formed of stainless steel 304.

Of course, other suitable guidewire dimensions and configurations can also be used. For example guidewires having an outer diameter of approximately 0.018 inches may also be used. For other coronary applications, different dimensions may also be used, such as outer diameters of approximately 0.010 inches to 0.014 inches. Further, it will be appreciated that the particular size of wire 346 will vary with application. Applications involving neural vasculature will require the use of a smaller guidewire, while other applications will require the use of a larger guidewire. Also, wire 346 can be replaced by a hollow guidewire, or hypotube of similar, or other suitable dimensions.

In addition, in order to make wire 342, hoop 346, or filter 344 radiopaque, other materials can be used. For example, radiopaque loaded powder can be used to form a polyurethane sheath which is fitted over wire 346 or hoop 342, or which is implemented in filter 344. Also, hoop 342 and wire 346 can be gold plated in order to increase radiopacity. Also, marker bands can be used on wire 346 or filter 344 to increase the radiopacity of the device.

In operation, hoop 342 (and thus filter 344) is preferably collapsed to a radially contracted position which more closely approximates the outer diameter of wire 346. Methods of performing this contraction are described later in the specification. Once retracted to a more low profile position, wire 346 is manipulated to position hoop 342 and filter 344 distal of a restriction to be treated. Then, the restraining force which is used to restrain hoop 342 in the predeployment, low profile position is removed, and the superelastic properties of nitinol hoop 342 (or the shape memory properties of another shape memory alloy) are utilized in allowing hoop 342 to assume its shape memory position. This causes hoop 342 to define a substantially lumen filling mouth to filter 344 which is positioned distal of the restriction to be treated.

A suitable dilatation device is then advanced over wire 346 and is used to treat the vascular restriction. Emboli which are carried by blood flow distal of the restriction are captured by filter 344. After the dilatation procedure, filter 344, along with the emboli retained therein, are retrieved from the vasculature. Various retrieval procedures and devices are described later in the specification.

By allowing hoop-shaped frame 342 to be unattached to wire 346, and only connected to wire 346 through filter 344 (or other super structure used to support filter 344), wire 346 is allowed to substantially float within hoop 342. This configuration provides some advantages. For instance, hoop 342 can better follow the vasculature without kinking or prolapsing (i.e., without collapsing upon itself). Thus, certain positioning or repositioning of filter 344 can be accomplished with less difficulty.

FIG. 21B illustrates a protection device 352 in accordance with another embodiment of the present invention. Protection device 352 is similar to protection device 340, and similar items are similarly numbered. However, rather than having simply a hoop-shaped frame 342 to support filter 344, and drive filter 344 into its expanded and deployed position, device 352 includes frame 354 which includes a hoop-shaped portion 356, and a pair of tails 358 and 360.

Tails 358 and 360 extend proximally from hoopshaped portion 356 to an attachment region 362. In the preferred embodiment, tails 358 and 360 are attached to wire 346 at attachment region 362 by soldering, welding, brazing, adhesive, or any other suitable attachment mechanism. In the embodiment shown in FIG. 21B, attachment sleeve 364, formed of a weldable material, is attached at its inner periphery to tails 358 and 360. Sleeve 364 is then attached, using welding or brazing, to wire 346.

By providing tails 358 and 360, frame 354 is directly connected to wire 346. However, tails 358 and 360 are provided so that the point of attachment of frame 354 to wire 346 is located several millimeters proximal of hoop-shaped portion 356. This provides some additional structural integrity to frame 354, but still allows frame 354 to substantially float about wire 346 in the region of hoop-shaped frame portion 356.

Figure 21C:
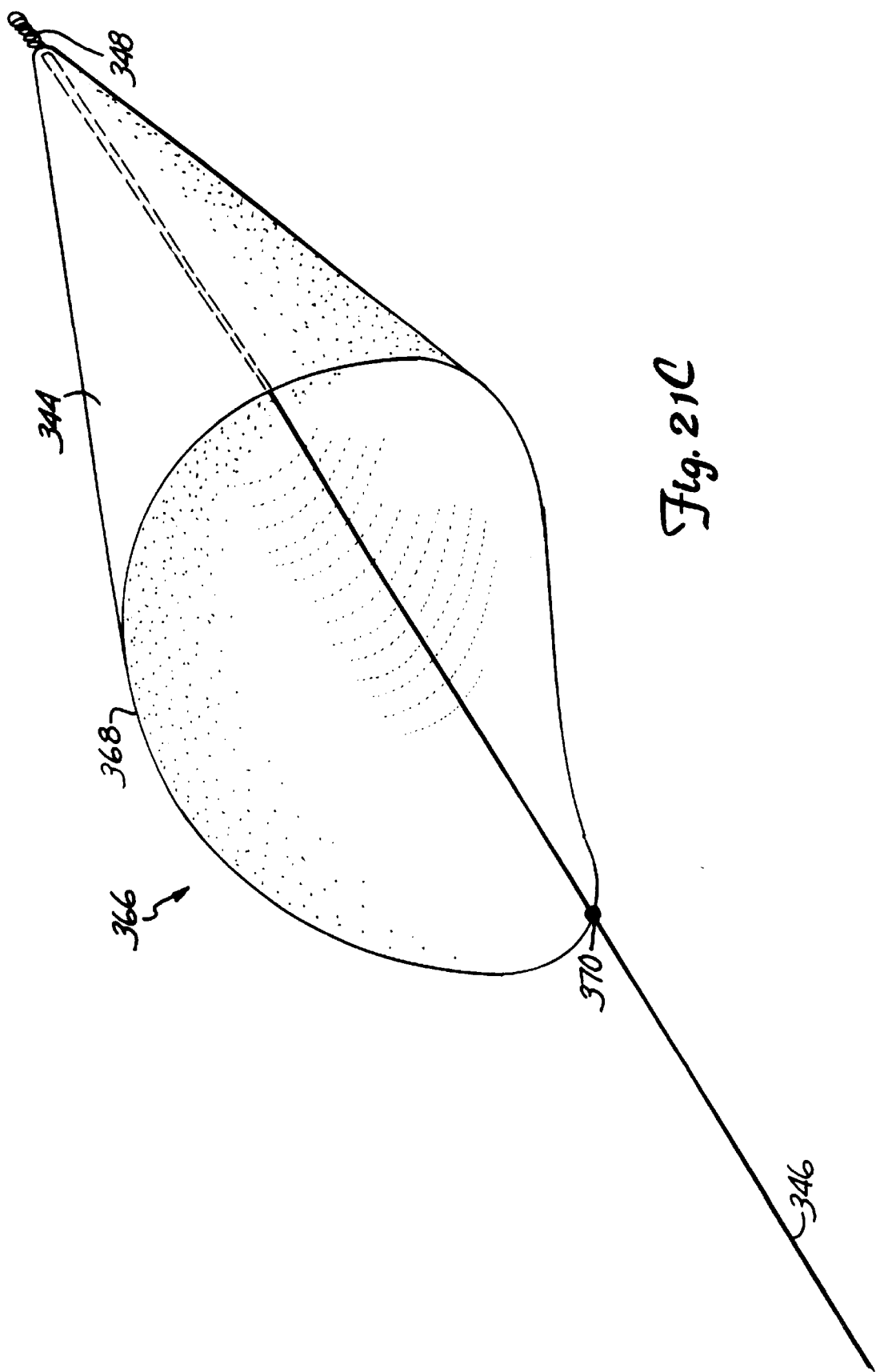

FIG. 21C illustrates a protection device 366 in accordance with another embodiment of the present invention. Protection device 366 is similar to protection devices 340 and 352 shown in FIGS. 21A and 21B, and similar items are similarly numbered. However, device 366 includes hoop-shaped frame 368. Frame 368 is similar to frame 342 shown in FIG. 21A. However, unlike frame 342, hoop 368 does not allow wire 346 to float freely therein. Instead, hoop 368 is directly attached to wire 346 at attachment point 370. This causes hoop-shaped frame 368 and filter 344 to reside eccentrically about wire 346.

FIGS. 22A–22C illustrate one preferred embodiment for delivering one of devices 340, 352 and 366. For the sake of clarity, only device 352 is illustrated in FIGS. 22A–22C.

FIG. 22A illustrates delivery device 372. In the preferred embodiment, delivery device 372 includes proximal hub 374, shaft 376, and distal retaining section 378. Also, in one preferred embodiment, device 372 also includes marker band 380. In the preferred embodiment, delivery device 372 is similar to a conventional balloon catheter in that proximal hub 374 is a conventional hub, and shaft 376 is a conventional balloon catheter shaft. Further, distal retaining section 378 is preferably a conventional angioplasty balloon having an inflated diameter of approximately 1.5 –2.0 millimeters, but having its distal end cutoff such that the distal end 382 of balloon 378 is open.

Prior to insertion of device 372 into the vasculature, hoop-shaped frame 354 is retracted into its low profile deployment position and is withdrawn through end 382 into balloon 378. Then, the distal end of balloon 378 is exposed to heat to heat shrink or heat set the distal end of balloon 378 around the radially retracted device 352. Device 372, including device 352, is then inserted in the vasculature either through a preplaced guide catheter, along with a guide catheter, or simply without a guide catheter utilizing coil tip 348.

In any case, once device 372 is properly placed such that balloon 378 is located distal of the restriction to be treated, distal protection device 352 is then removed from within heat collapsed balloon 378. In one preferred embodiment, the physician simply accomplishes longitudinal movement of wire 346 relative to catheter 376. For instance, the physician may simply hold wire 346 longitudinally in place and withdraw catheter 376 proximally relative to wire 346 by pulling on hub 374. This causes balloon 378 to move proximally relative to device 352, and thereby to expose device 352 to the vasculature.

FIG. 22B illustrates another preferred embodiment for removing device 352 from within balloon 378. In the embodiment shown in FIG. 22B, syringe 384, which contains fluid, is inserted into coupling 386 in hub 374. The physician then introduces pressurized fluid into the lumen of catheter 376. The pressurized fluid advances down the lumen of catheter 376 to the distal end where it encounters collapsed balloon 378. The pressure exerted on balloon 378 by the pressurized fluid causes balloon 378 to open radially. Then, the physician withdraws catheter 376 relative to device 352 thereby exposing device 352 to the vasculature.

In any case, once device 352 is no longer restrained by balloon 378, device 352 assumes its shape memory position in the vasculature, as illustrated in FIG. 22C. Thus, device 352 substantially forms a lumen-filling basket or filter which allows blood to pass distally therethrough, but which retains or captures embolic material carried by the blood flow. The physician then simply removes device 372 from the vasculature, leaving device 352 in place during subsequent procedures. In one preferred embodiment, shaft 376 includes a predefined slit or score from a region just proximal of marker band 380 to, or through, hub 374. Thus, as the physician removes device 372, it can be peeled away from device 352. Also, or alternatively, device 372 can be provided with an aperture in shaft 376 near its distal end. The proximal end of wire 346 will thus lie outside of shaft 376. Wire 346 can enter shaft 376 through the aperture and extend through the distal end of shaft 376. This also facilitates easier withdrawal of device 372 over wire 346.

Figure 23D:
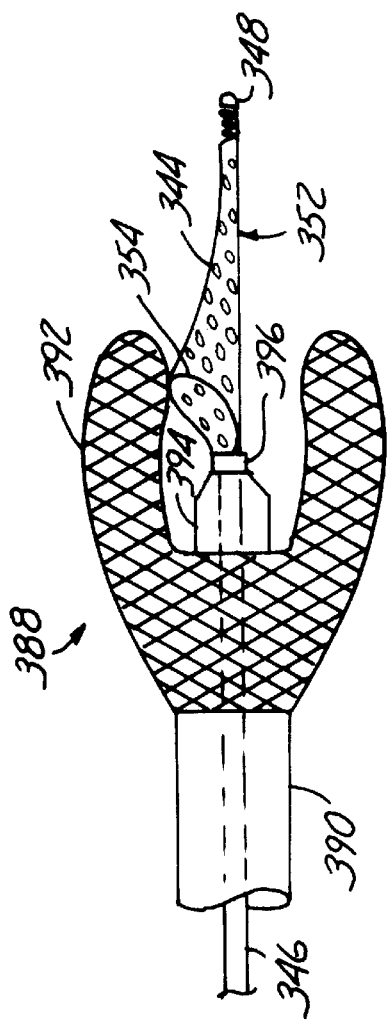

FIGS. 23A–23E illustrate one preferred embodiment for retrieving one of the devices 340, 352 and 366 described in FIGS. 21A–21C. For the sake of clarity, only device 352 is illustrated in FIGS. 23A–23E. FIG. 23A illustrates retrieval device 388. Retrieval device 388 is preferably formed of proximal shaft 390, mesh portion 392, and end cap 394. Items 390, 392 and 394 preferably each have lumens therein to define a passageway for receiving wire 346. Also, wire 346 may optionally be provided with an positive stop 396 (which can be embodied as a radiopaque marker band). Optional stop 396 may also simply be an annular ring attached to wire 346 proximate to filter 344, or may be any other suitable stop.

Proximal shaft 390 is preferably simply a polymer or nitinol tube sized and configured to track over wire 346. End cap 394 is also preferably formed to track over wire 346, but also contains radiopaque material to serve as a distal marker band for retrieval device 388. Mesh 392 is preferably a braid or mesh formed of wire or polymer material having sufficient flexibility that it can be deflected as described below.

Mesh 392 preferably has a proximal end coupled to proximal shaft 390, by adhesive, welding, or other suitable attachment mechanisms. Mesh 392 also preferably includes a distal end connected to end cap 394, also by a suitable connection mechanism.

In order to retrieve filter 344, which likely contains embolic material, device 388 is inserted in the low profile position shown in FIG. 23A, over wire 346, to a position proximate filter 344. Then, device 388 is advanced toward filter 344, until end cap 394 abuts positive stop 396, or the hoop-shaped frame 354. Continued advancement of proximal shaft 390 relative to wire 346 causes compression of mesh 392. This results in a radial expansion of an intermediate portion of mesh 392 (between the proximal and distal ends of mesh 392). The radial expansion of mesh portion 392 is illustrated in FIG. 23B.

Figure 23E:
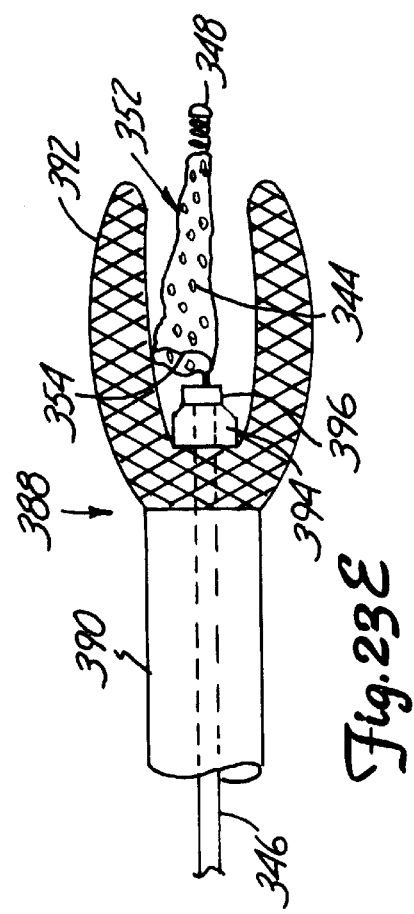

By continuing to advance proximal shaft 390 relative to wire 346, the intermediate portion of mesh 392 is configured to bend over on itself such that it is axially displaced toward filter 344, in the direction generally indicated by arrows 398 in FIG. 23C. In the preferred embodiment, mesh 392 is sized and configured such that, with continued advancement of proximal shaft 390 relative to wire 346, this action continues as shown in FIGS. 23D and 23E until the intermediate portion of mesh 392 encompasses at least the mouth of filter 344. Also, in the preferred embodiment, the intermediate portion of mesh 392, when driven as described above, engages and contracts the mouth of filter 344 to a lower profile position, such as that shown in FIG. 23E. In yet another preferred embodiment, mesh 392 is sized and configured to substantially engulf the entire filter 344.

Once at least the mouth of filter 344 is encompassed by mesh 392, device 388, along with device 352, are simply withdrawn from the vasculature. In one preferred embodiment in which a guide catheter is used, devices 388 and 352 are simply withdrawn either into the guide catheter and the guide catheter is removed with those devices, simultaneously, or devices 388 and 352 are removed from the guide catheter prior to removal of the guide catheter. In another preferred embodiment, in which no guide catheter is used, devices 388 and 352 are simply removed from the vasculature simultaneously.

It will also be appreciated, of course, that rather than providing device 388 with a single proximal tube 390 and end cap 394, a second actuation tube or wire can also be provided which is attached to end cap 394, and which extends back through the lumen in proximal tube 390 and is longitudinally movable relative to proximal shaft 390. In that way, the actuation wire or elongate member can be used to pull cap 394 closer to the distal portion of proximal shaft 390 in order to accomplish the action illustrated in FIGS. 23A–23E. This feature is also illustrated in FIGS. 18A–18D which illustrate the mesh portion folded proximally rather than distally.

FIGS. 24A–24C illustrate another preferred embodiment in accordance with the present invention, for retrieving any of the distal protection devices 340, 352 or 366 shown in FIGS. 21A–21C. For the sake of clarity, only device 352 is illustrated in FIGS. 24A–24C.

FIG. 24A illustrates retrieval device 400. Retrieval device 400 preferably includes retrieval sheath 402, proximal locking device 404, dilator sheath 405, and nose cone 406. In the preferred embodiment, retrieval sheath 402 is preferably formed of polyether block amide (PEBAX) material having an outer diameter of approximately six French (i.e., approximately 2 mm) and having a shore D hardness of approximately 40. Also, retrieval sheath 402 preferably has a wall thickness of approximately 0.004 inches. Dilator sheath 405, and nose cone 406, are preferably formed of low density polyethylene, or high density polyethylene. Sheath 405 preferably has an outer diameter which is approximately equal to the inner diameter of sheath 402. In addition, the inner diameter of sheath 405 and nose cone 406 is preferably just large enough to fit over, and track over, wire 346. Nose cone 406 preferably has a proximal portion which is either attached to, or formed integrally with, sheath 405. The outer diameter of the proximal portion of nose cone 406 is also approximately the same as the outer diameter of sheath 405. However, nose cone 406 also preferably has a distal portion which tapers, or reduces along preferably a smooth curve, to an outer diameter which terminates at the inner diameter of nose cone 406.

Proximal locking device 404 is preferably any suitable, and commercially available, locking device which can be configured to lock dilator sheath 405 to guidewire 346.

In order to retrieve device 352 from the vasculature, device 400 is preferably advanced over guidewire 346 to a position shown in FIG. 24B, in which the distal portion of nose cone 406 is closely proximate, or adjacent to, either optional stop 396 or the mouth of filter 344. Then, proximal locking device 404 is actuated to lock dilator sheath 405 to wire 346 so that wire 346 and dilator sheath 405 (as well as nose cone 406) can be moved as a unitary piece.

Next, wire 346 (and hence dilator sheath 405 and nose cone 406) are withdrawn longitudinally relative to retrieval sheath 402. This causes the mouth of filter 344 to enter within the distal opening in retrieval sheath 402. This results in device 352 being positioned relative to sheath 402 as shown in FIG. 24C. Of course, wire 346, dilator sheath 405 and nose cone 406 can be withdrawn further into sheath 402 such that the entire filter 344, and wire tip 348, are disposed within the lumen of sheath 402.

In any case, once at least the mouth of filter 344 is within sheath 402, device 352 is configured to be removed from the vasculature. This can be accomplished by either removing dilator sheath 405, nose cone 406 and device 352 as a unitary piece, leaving sheath 402 in place for later removal, or by removing sheath 402 with the remainder of the system, either through a guide catheter or simply through the vasculature, simultaneously. Also, where a guide catheter is used, device 352 and device 400 can be removed through the guide catheter leaving the guide catheter in place, or the guide catheter can be removed simultaneously with the other devices 352 and 400.

It should be noted that all of the devices according to the present invention can optionally be coated with an antithrombotic material, such as heparin (commercially available under the tradename Duraflow from Baxter), to inhibit clotting.

Thus, in accordance with one preferred embodiment of the present invention, the superelastic properties of nitinol are used to form a frame at least in the area of the mouth of the distal protection filter. Thus, the distal protection device can be deployed, retrieved, and re-deployed any number of times without incurring plastic deformation. In addition, in other preferred embodiments in accordance with the present invention, various deployment and retrieval techniques and systems are provided which address various problems associated with such systems.

Although the present invention has been described with reference to preferred embodiments, workers skilled in the art will recognize that changes may be made in form and detail without departing from the spirit and scope of the invention.

What is claimed is:

1. An emboli capturing system for capturing emboli in a body lumen, comprising:

a first elongate member having a proximal end and a distal end;

an expandable emboli capturing device mounted proximate the distal end of the first elongate member, the emboli capturing device being movable between a radially expanded position and a radially retracted position, the expandable emboli capturing device forming a basket with a proximally opening mouth when in the radially expanded position;

a second elongate member having a proximal end and a distal end and a lumen extending between the proximal and distal ends, the lumen being sized to slidably receive a portion of the first elongate member therein; and an expandable delivery device mounted to the distal end of the second elongate member and being movable from a radially retracted position to a radially expanded position, the delivery device having a receiving end configured to receive the emboli capturing device, the delivery device retaining at least the mouth of the emboli capturing device in the radially retracted position when the delivery device is in the radially retracted position, the emboli capturing device being longitudinally movable out from within the delivery device when the delivery device is in the radially expanded position.

2. The emboli capturing system of claim 1 and further comprising:

a retrieval device, configured to be longitudinally movable relative to the emboli capturing device in the body lumen and having a receiving end configured to receive at least the mouth of the emboli capturing device when the emboli capturing device is in the radially expanded position.

3. The emboli capturing system of claim 2 wherein the retrieval device comprises the expandable delivery device in the radially expanded position.

4. The emboli capturing system of claim 2 wherein the receiving end of the retrieval device is contractible from a radially expanded position to a radially contracted position to at least partially collapse the emboli capturing device therein.

5. The emboli capturing system of claim 4 wherein the retrieval device comprises:

a third elongate member having proximal and distal ends and a lumen extending therebetween, the lumen being sized to slidably receive at least a portion of the first elongate member therein, the lumen at the distal end of the third elongate member forming the receiving end and being sized to receive a most radially expanded portion of the emboli capturing device; and a fourth elongate member movable within the lumen of the third elongate member, the fourth elongate member having an intermediate region sized to substantially fill the receiving end and a distal tip having an outer diameter less than an outer diameter of the intermediate region.

6. The emboli capturing system of claim 5 wherein the distal tip of the fourth elongate member is configured with an aperture therein sized to track over the first elongate member.

7. The emboli capturing system of claim 6 wherein the fourth elongate member is formed in a substantially conical shape between the distal tip thereof and the intermediate region thereof.

8. The emboli capturing system of claim 2 wherein the retrieval device includes:

a third elongate member having proximal and distal ends and a lumen extending therebetween, the lumen being sized to slidably receive at least a portion of the first elongate member; and a mesh sleeve having a first end coupled to the third elongate member, a second end distal of the first end and an intermediate portion between the first and second ends, the mesh sleeve being configured such that relative longitudinal movement of one of the first and second ends thereof relative to another of the first and second ends thereof drives movement of the mesh portion from a radially retracted position, to a radially expanded position in which the intermediate portion expands radially outward relative to the first and second ends, and to a collapsed position in which the mesh sleeve bends such that the intermediate portion is displaced in a direction toward one of the first and second ends of the mesh sleeve.

9. The emboli capturing system of claim 8 wherein the retrieval device is configured such that sufficient longitudinal movement of the emboli capturing device toward the mesh sleeve causes the emboli capturing device to drive the second end of the mesh sleeve toward the first end of the mesh sleeve.

10. The emboli capturing system of claim 9 wherein the mesh sleeve is sized to encompass at least the mouth of the emboli capturing device as the mesh sleeve moves from the radially expanded position to the collapsed position.

11. The emboli capturing system of claim 2 wherein the retrieval device includes:

a third elongate member having proximal and distal ends and a lumen extending therebetween, the lumen being sized to slidably receive at least a portion of the first elongate member;

a fourth elongate member longitudinally movable relative to the third elongate member; and a mesh sleeve having a first end coupled to the third elongate member and a second end coupled to the fourth elongate member and an intermediate portion between the first and second ends, the mesh sleeve being configured such that relative longitudinal movement of one of the third and fourth elongate members relative to another of the third and fourth elongate members drives movement of the mesh portion from a radially retracted position, to a radially expanded position in which the intermediate portion expands radially outward relative to the first and second ends, and to a collapsed position in which the mesh sleeve bends such that the intermediate portion is displaced in a direction toward one of the first and second ends of the mesh sleeve.

12. The emboli capturing system of claim 1 wherein the receiving end of the delivery device is defined by a portion of a dilatation balloon.

13. The emboli capturing system of claim 1 wherein the receiving end of the delivery device is thermally shrunk over at least the mouth of the emboli capturing device to retain the emboli capturing device in the radially contracted position during delivery.

14. The emboli capturing system of claim 1 wherein the receiving end of the delivery device is movable from the radially retracted position to the radially expanded position by delivery of pressurized fluid through the lumen in the second elongate member.

15. The emboli capturing system of claim 1 wherein the emboli capturing device is a self-expanding device biased in the radially expanded position.

16. The emboli capturing system of claim 15 wherein the emboli capturing device includes:
    a frame formed of a shape memory alloy; and
    a filter portion supported by the frame, the filter portion being configured to permit blood flow therethrough and to capture emboli carried by blood flow therethrough.

17. The emboli capturing system of claim 16 wherein the filter portion has a first end connected to the first elongate member and a second end connected to the frame and wherein the frame comprises:
    a loop disposed about the first elongate member to define the mouth of the emboli capturing device.

18. The emboli capturing system of claim 17 wherein the loop is directly connected to the first elongate member.

19. The emboli capturing system of claim 17 wherein the shape memory alloy comprises an alloy having superelastic properties.

20. The emboli capturing system of claim 19 wherein the shape memory alloy includes nitinol.

21. The emboli capturing system of claim 20 wherein the emboli capturing device is substantially conical in shape.

22. The emboli capturing system of claim 21 wherein the filter portion comprises a polyurethane member having a plurality of holes therein.

23. The emboli capturing system of claim 1 wherein the first elongate member comprises a guidewire.

24. A method of capturing emboli carried by flow of fluid through a body lumen, the method comprising:
    providing a first elongate member having a proximal end and a distal end;
    providing an expandable emboli capturing device mounted proximate the distal end of the first elongate member, the emboli capturing device being movable between a radially expanded position and a radially retracted position, the expandable emboli capturing device defining a proximally opening mouth when in the radially expanded position;
    providing a second elongate member having a proximal end and a distal end and a lumen extending between the proximal and distal ends, the lumen being sized to slidably receive a portion of the first elongate member therein;
    providing an expandable delivery device mounted to the distal end of the second elongate member and being movable from a radially retracted position to a radially expanded position, the delivery device having a receiving end configured to receive the emboli capturing device, the delivery device retaining at least the mouth of the emboli capturing device in the radially retracted position when the delivery device is in the radially retracted position;
    inserting the expandable delivery device into the lumen with the mouth of the emboli capturing device retained in the radially retracted position within the delivery device;
    expanding the expandable delivery device into the radially expanded position; and
    longitudinally moving the delivery device relative to the emboli capturing device to remove the emboli capturing device from within the delivery device.

25. The method of claim 24 and further comprising:
    providing a retrieval device, configured to be longitudinally movable relative to the emboli capturing device in the body lumen and having a receiving end configured to receive at least the mouth of the emboli capturing device when the emboli capturing device is in the radially expanded position; and
    longitudinally moving the delivery device relative to the emboli capturing device such that at least the mouth of the emboli capturing device is in the receiving end of the retrieval device.

26. The method of claim 25 wherein the receiving end of the retrieval device is contractible from a radially expanded position to a radially contracted position, and further comprising:
    contracting the receiving end of the retrieval device to at least partially collapse the emboli capturing device therein.

27. The method of claim 26 wherein providing a retrieval device comprises:
    providing a third elongate member having proximal and distal ends and a lumen extending therebetween, the lumen being sized to slidably receive at least a portion of the first elongate member therein, the lumen at the distal end of the third elongate member forming the receiving end and being sized to receive a most radially expanded portion of the emboli capturing device;
    providing a fourth elongate member movable within the lumen of the third elongate member, the fourth elongate member having an intermediate region sized to substantially fill the receiving end and a distal tip having an outer diameter less than an outer diameter of the intermediate region;
    advancing the third and fourth elongate members over the first elongate member, with the intermediate region of the fourth elongate member positioned within the third elongate member to fill the receiving end thereof, to a point proximate the emboli capturing device;
    withdrawing the distal tip of the fourth elongate member within the lumen of the third elongate member; and
    positioning at least the mouth of the emboli capturing device within the receiving end of the retrieval device.

28. The method of claim 27 and further comprising:
    withdrawing the first, third, and fourth elongate members from the body lumen.

29. The method of claim 25 wherein providing the retrieval device includes:

providing a third elongate member having proximal and distal ends and a lumen extending therebetween, the lumen being sized to slidably receive at least a portion of the first elongate member;

providing a mesh sleeve having a first end coupled to the third elongate member, a second end distal of the first end and an intermediate portion between the first and second ends, the mesh sleeve being configured such that relative longitudinal movement of one of the first and second ends thereof relative to another of the first and second ends thereof drives movement of the mesh portion from a radially retracted position, to a radially expanded position in which the intermediate portion expands radially outward relative to the first and second ends, and to a collapsed position in which the mesh sleeve bends such that the intermediate portion is displaced in a direction toward one of the first and second ends of the mesh sleeve;

advancing the third elongate member into the body lumen over the first elongate member to a point proximate the mouth of the emboli capturing device; and accomplishing relative longitudinal movement of the emboli capturing device and the mesh sleeve toward one another, driving the second end of the mesh sleeve toward the first end of the mesh sleeve such that the mesh sleeve encompasses at least the mouth of the emboli capturing device as the mesh sleeve moves from the radially expanded position to the collapsed position.

30. The method of claim 24 wherein expanding comprises:

delivering pressurized fluid through the lumen in the second elongate member.

* * * * *